(12) United States Patent
Takeuchi et al.

(10) Patent No.: US 10,368,583 B2
(45) Date of Patent: Aug. 6, 2019

(54) NON-BURNING-TYPE FLAVOR INHALER

(71) Applicant: JAPAN TOBACCO INC., Tokyo (JP)

(72) Inventors: Manabu Takeuchi, Tokyo (JP);
Akihiko Suzuki, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 339 days.

(21) Appl. No.: 15/340,175

(22) Filed: Nov. 1, 2016

(65) Prior Publication Data

US 2017/0042252 A1     Feb. 16, 2017

Related U.S. Application Data

(63) Continuation of application No. PCT/JP2015/063036, filed on Apr. 30, 2015.

(30) Foreign Application Priority Data

May 2, 2014    (JP) .................................. 2014-095164

(51) Int. Cl.
*A24F 47/00*      (2006.01)
*A24F 7/02*       (2006.01)
(Continued)

(52) U.S. Cl.
CPC .............. *A24F 47/008* (2013.01); *A24F 7/02* (2013.01); *A24F 47/00* (2013.01); *A61M 11/042* (2014.02);
(Continued)

(58) Field of Classification Search
CPC ..................................................... A24F 47/008
See application file for complete search history.

(56) References Cited

U.S. PATENT DOCUMENTS 5,134,886 A    8/1992  Ball
9,854,841 B2 * 1/2018  Ampolini .............. A24F 47/008
(Continued)

FOREIGN PATENT DOCUMENTS

CN    102227175 A    10/2011
CN    102264420 A    11/2011
(Continued)

OTHER PUBLICATIONS

Extended European Search Report for European Application No. 15785600.6, dated Dec. 20, 2017.
(Continued)

*Primary Examiner* — Robert A Hopkins
(74) *Attorney, Agent, or Firm* — Birch, Stewart, Kolasch & Birch, LLP

(57) ABSTRACT

A non-burning type flavor inhaler comprises: a housing having an air flow path that continues from an inlet to an outlet; an atomizer configured to atomize an aerosol source without burning; a sensor configured to output a value that changes in accordance with a puff action of a user; and a controller configured to detect a puff action of the user when a response value derived from a value that is output from the sensor satisfies an inhaling condition, the controller configured to identify that the user is an authorized user when the response value satisfies an identification condition that is different from the inhaling condition.

20 Claims, 17 Drawing Sheets

(51) Int. Cl.
*H05B 1/02* (2006.01)
*A61M 15/06* (2006.01)
*A61M 11/04* (2006.01)

(52) U.S. Cl.
CPC ........... *A61M 15/06* (2013.01); *H05B 1/0244* (2013.01); *A61M 2205/27* (2013.01); *A61M 2205/3653* (2013.01); *A61M 2205/50* (2013.01); *A61M 2205/587* (2013.01); *A61M 2205/60* (2013.01); *A61M 2205/8206* (2013.01); *H05B 2203/021* (2013.01)

(56) References Cited

U.S. PATENT DOCUMENTS

| | | | |
|---|---|---|---|
| 10,159,279 | B2 * | 12/2018 | Lord .................... G06F 1/3296 |
| 2008/0092912 | A1 | 4/2008 | Robinson et al. |
| 2011/0226236 | A1 | 9/2011 | Buchberger |
| 2012/0186594 | A1 | 7/2012 | Liu |
| 2012/0199146 | A1 | 8/2012 | Marangos |
| 2013/0284192 | A1 | 10/2013 | Peleg et al. |
| 2013/0319439 | A1 | 12/2013 | Gorelick et al. |

FOREIGN PATENT DOCUMENTS

| | | |
|---|---|---|
| CN | 103948177 A | 7/2014 |
| EP | 2460423 A1 | 6/2012 |
| JP | H07-124259 A | 5/1995 |
| JP | 2010-506594 A | 3/2010 |
| JP | 2013-526834 A | 6/2013 |
| WO | WO 2012/072790 A1 | 6/2012 |
| WO | WO 2013/016846 A1 | 2/2013 |
| WO | WO 2013/034456 A1 | 3/2013 |
| WO | WO 2013/060784 A2 | 5/2013 |
| WO | WO 2014/037259 A1 | 3/2014 |
| WO | WO 2014/054035 A1 | 4/2014 |
| WO | WO 2014/058678 A1 | 4/2014 |
| WO | WO 2014/150704 A2 | 9/2014 |

OTHER PUBLICATIONS

Extended European Search Report for European Application No. 15785768.1, dated Dec. 20, 2017.
International Search Report for PCT/JP2015/063040 (PCT/ISA/210) dated Jul. 21, 2015.
U.S. Office Action dated Dec. 20, 2018 for U.S. Appl. No. 15/340,054.
International Search Report for for PCT/JP2015/063036 (PCT/ISA/210) dated Aug. 4, 2015.

* cited by examiner

FIG. 6

| PUFFING STATE | NON-PUFFING STATE #1 | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | END LIGHT-EMITTING MODE | LIGHT-EMITTING MODE #1 |

FIG. 7

| PUFFING STATE | NON-PUFFING STATE #1 | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | END LIGHT-EMITTING MODE | LIGHT-EMITTING MODE #1-4 |

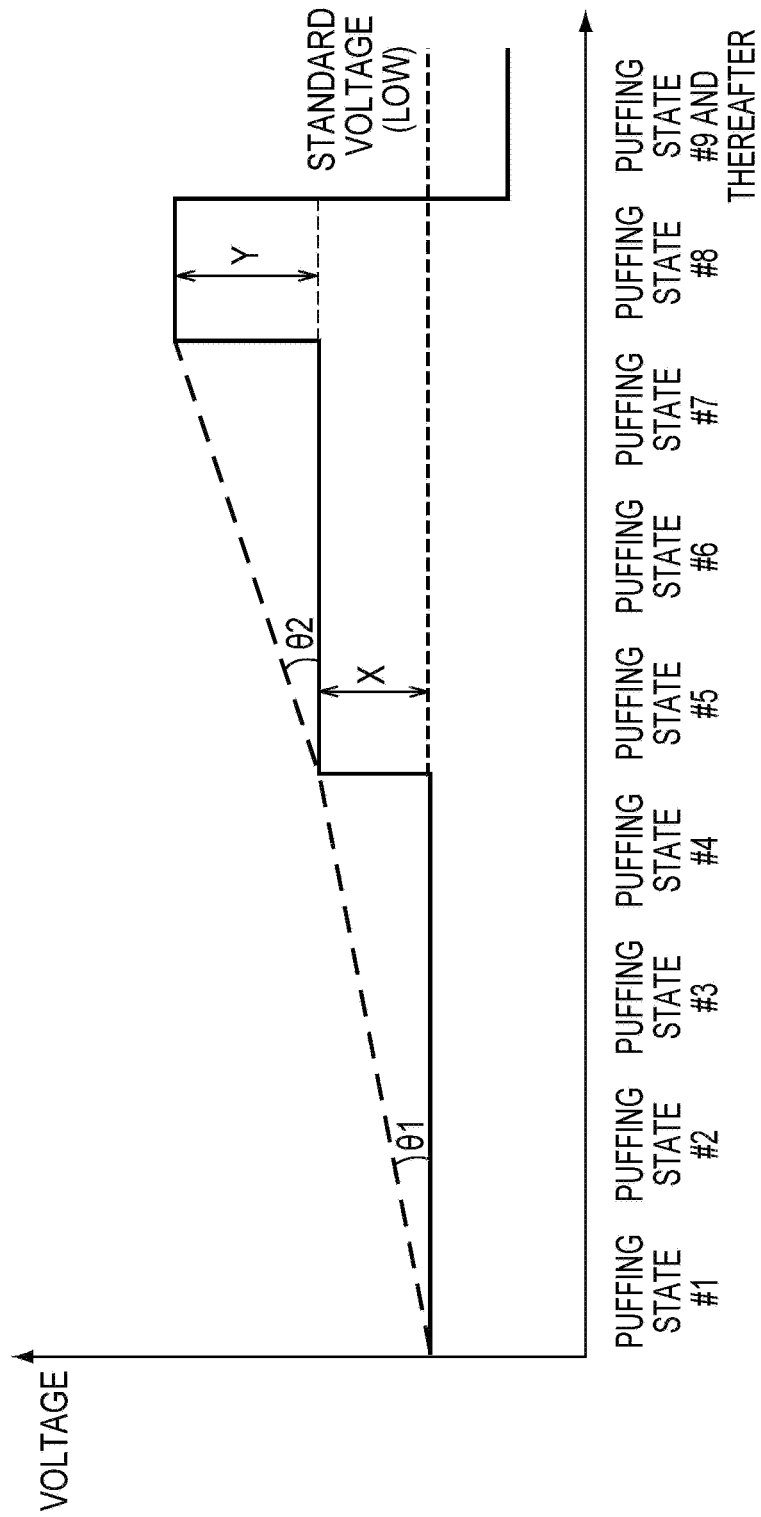

NON-BURNING-TYPE FLAVOR INHALER

CROSS REFERENCE TO RELATED APPLICATIONS

This application is a Continuation of PCT International Application No. PCT/JP2015/063036, filed on Apr. 30, 2015, which claims priority under 35 U.S.C. 119(a) to Patent Application No. 2014-095164, filed in Japan on May 2, 2014, all of which are hereby expressly incorporated by reference into the present application.

TECHNICAL FIELD

The present invention relates to a non-burning type flavor inhaler having an atomizer configured to atomize an aerosol source without burning.

BACKGROUND ART

Conventionally, there is known a non-burning type flavor inhaler for inhaling flavor without burning. The non-burning type flavor inhaler has an atomizer configured to atomize an aerosol source without burning.

By applying a user identification technique to such a non-burning type flavor inhaler, a technique for preventing the use of the non-burning type flavor inhaler by an unidentified user has been proposed (For example, Patent Documents 1 and 2).

PRIOR ART DOCUMENT

Patent Document

Patent Document 1: CN103948177
Patent Document 2: WO2014/150704

SUMMARY

A first feature is summarized as a non-burning type flavor inhaler, comprising: a housing having an air flow path that continues from an inlet to an outlet; an atomizer configured to atomize an aerosol source without burning; a sensor configured to output a value that changes in accordance with a puff action of a user; and a controller configured to detect a puff action of the user when a response value derived from a value that is output from the sensor satisfies an inhaling condition, the controller configured to identify that the user is an authorized user when the response value satisfies an identification condition that is different from the inhaling condition.

A second feature according to the first feature is summarized as that the controller determines, for each one-time puff action, whether or not the inhaling condition is satisfied and whether or not the identification condition is satisfied.

A third feature according to the first feature or the second feature is summarized as that the controller determines whether or not the identification condition is satisfied after the inhaling condition is satisfied.

A fourth feature according to any one of the first feature to the third feature is summarized as that the controller determines, on the basis of an inclination configured by two or more of the response values or an absolute value of the response value, whether or not at least one of the inhaling condition and the identification condition is satisfied.

A fifth feature according to the first feature is summarized as that the inhaling condition is that the absolute value exceeds a predetermined absolute value, and that the identification condition is that the inclination exceeds a predetermined inclination.

A sixth feature according to the fourth feature is summarized as that the inhaling condition is that an absolute value of the response value exceeds a first absolute value, and that the identification condition is that an absolute value of the response value exceeds a second absolute value that is larger than the first absolute value.

A seventh feature according to any one of the first feature to the sixth feature is summarized as that the controller uses a first identification condition as the identification condition in a first puff action, and uses a second identification condition that is different from the first identification condition as the identification condition in a second puff action performed after the first identification condition is satisfied.

A eighth feature according to the seventh feature is summarized as that the controller uses the first identification condition when a specific condition is satisfied after the first identification condition is satisfied.

A ninth feature according to any one of the first feature to the eighth feature is summarized as that the controller starts a supply of power source output to the atomizer when the identification condition is satisfied.

A tenth feature according to any one of the first feature to the eighth feature is summarized as that the controller starts a supply of power source output to the atomizer when the inhaling condition is satisfied, and the controller stops the supply of the power source output to the atomizer when the identification condition is not satisfied after the inhaling condition is satisfied.

A eleventh feature according to the first feature is summarized as that the controller has an action mode by which a supply of power source output to the atomizer is performed on the basis of the response value, and an identification mode by which it is determined, on the basis of the response value, whether or not the identification condition is satisfied, and the action mode starts after the identification condition is satisfied in the identification mode.

A twelfth feature according to the eleventh feature is summarized as that in the identification mode, the controller determines whether or not the identification condition is satisfied, on the basis of whether or not a profile represented by two or more of the response values in a space defined by a first axis indicating a dimension of the response value and a second axis indicating a time length corresponds to an identification profile.

A thirteenth feature according to the twelfth feature is summarized as that the identification profile is either registered beforehand or registered by the user.

A fourteenth feature according to any one of the eleventh feature to the thirteenth feature is summarized as that the controller ends the action mode when a profile represented by two or more of the response values in a space defined by a first axis indicating a dimension of the response value and a second axis indicating a time length corresponds to a cancellation profile.

A fifteenth feature according to any one of the eleventh feature to the fourteenth feature is summarized as that the controller resets the identification profile when a profile represented by two or more of the response values in a space defined by a first axis indicating a dimension of the response value and a second axis indicating a time length corresponds to a reset profile.

A sixteenth feature according to the fourteenth feature or the fifteenth feature is summarized as that the cancellation profile or the reset profile is the identification profile.

A seventeenth feature according to any one of the twelfth feature to the sixteenth feature is summarized as comprising a notification portion configured to notify a user of the identification profile, the cancellation profile or the reset profile.

A eighteenth feature according to any one of the twelfth feature to the seventeenth feature is summarized as that the controller determines, on the basis of a stringency selected from among a plurality of stages of stringency, whether or not the profile corresponds to the identification profile, the cancellation profile or the reset profile, and the flavor inhaler comprises an operation interface for switching the plurality of stages of stringency.

A nineteenth feature according to any one of the twelfth feature to the eighteenth feature is summarized as that the identification profile, the cancellation profile or the reset profile is defined by an absolute value of the response value, by whether or not the response value is a value based on inhaling, by whether or not the response value is a value based on blowing, by a sampling cycle of the response value, or by one or more parameters selected from among these parameters.

A twentieth feature according to any one of the twelfth feature to the nineteenth feature is summarized as that the non-burning type flavor inhaler comprises a mouthpiece member configured to be replaceable with respect to the housing, wherein the mouthpiece member comprises a memory configured to store the identification profile.

In the above-described features, "the identification condition differs from the response condition" may imply that the determination criteria (for example, a threshold value, or a value comparable with the threshold value) of whether or not the identification condition is satisfied is different from the determination criteria (for example, a threshold value, or a value comparable with the threshold value) of whether or not the inhaling condition is satisfied, or may imply that the determination timing of whether or not the identification condition is satisfied is different from the determination timing of whether or not the inhaling condition is satisfied.

In the above-described features, the second identification condition is preferably a condition that is satisfied more easily than the first identification condition. In particular, the second identification condition may be a condition that is satisfied easily at a stage earlier than the first identification condition, in a one-time puff action. Alternatively, the second identification condition may be a condition that is satisfied easily in a continuous manner as compared to the first identification condition, in different puff actions.

In the above-described features, the controller preferably starts the supply of power source output to the atomizer when the inhaling condition is satisfied, and the controller continues the supply of power source output to the atomizer when the identification condition is satisfied after the inhaling condition is satisfied.

In the above-described features, the non-burning type flavor inhaler preferably notifies the user whether or not at least the inhaling condition is satisfied. For example, the controller is capable of making the light-emitting element emit light in the first mode when the inhaling condition is satisfied. Further, the controller may make the light-emitting element emit light in the second mode when the identification condition is also satisfied. The first mode may be same as the second mode, or may be different from the second mode.

BRIEF DESCRIPTION OF THE DRAWINGS

FIG. 6 is a diagram showing an example of a light emitting mode according to the first embodiment.

FIG. 7 is a diagram showing an example of the light emitting mode according to the first embodiment.

FIG. 8 is a diagram showing an example of power control in a puff action series according to the first embodiment.

DESCRIPTION OF THE EMBODIMENT

Figure 1:
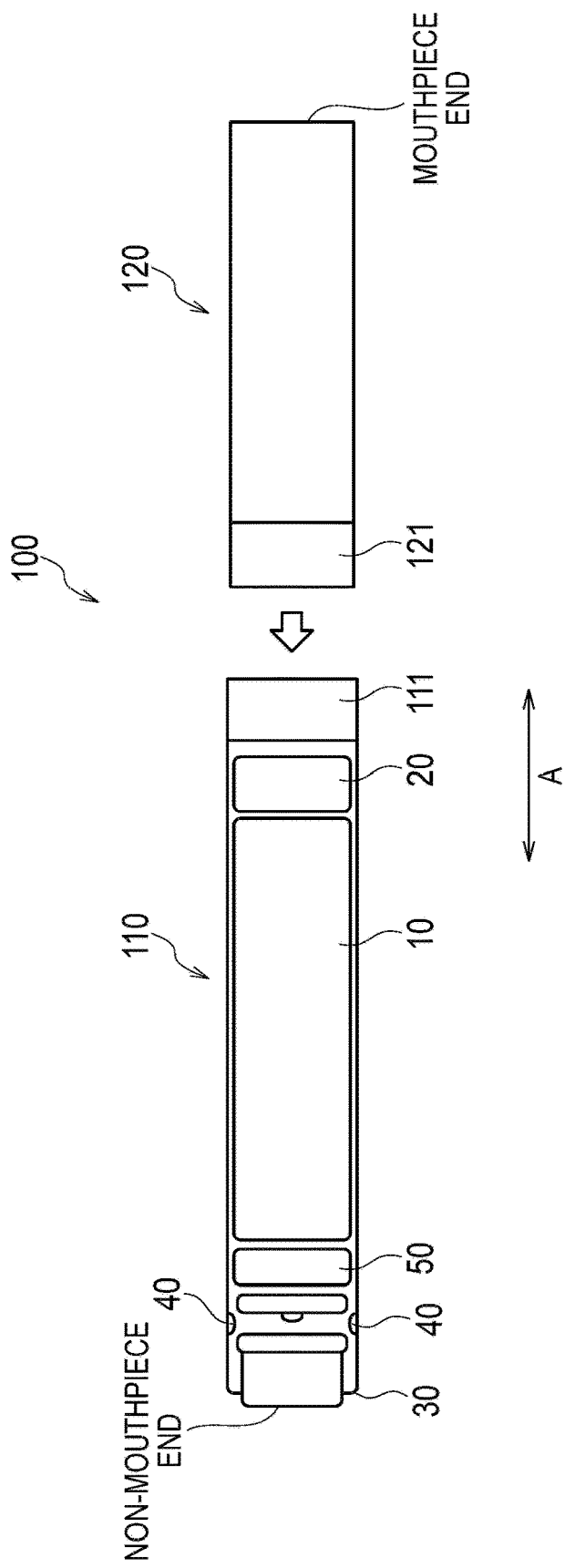
FIG. 1 is a diagram showing a non-burning type flavor inhaler 100 according to a first embodiment.

Hereinafter, the embodiments of the present invention will be described. In the following drawings, identical or similar components are denoted by identical or similar reference numerals. However, it should be noted that the drawings are schematic, and the ratio and the like of each of the dimensions is different from the reality.

Therefore, specific dimensions should be determined with reference to the description below. It is needless to mention that different relationships and ratio of dimensions may be included in different drawings.

Overview of Embodiment

In the non-burning type flavor inhaler mentioned in BACKGROUND ART, it is necessary to install a component specializing in the implementation of user identification, such as fingerprint identification, in the non-burning type flavor inhaler. However, from the viewpoint of reduction in the size or cost-saving of the non-burning type flavor inhaler, the number of components configuring the non-burning type flavor inhaler is preferably small.

The non-burning type flavor inhaler according to the embodiment includes a housing having an air flow path that continues from an inlet to an outlet; an atomizer configured to atomize an aerosol source without burning; a sensor configured to output a value that changes in accordance with a puff action of a user; and a controller configured to detect a puff action of the user when a response value derived from a value output from the sensor satisfies an inhaling condition, and configured to identify that the user is an authorized user when the response value satisfies an identification condition that is different from the inhaling condition.

In the embodiment, the controller detects a puff action of the user when the response value satisfies the inhaling condition, and the controller identifies that the user is an authorized user when the response value satisfies the identification condition. Since user identification is performed by using the sensor for detecting the puff action, it is possible to implement user identification while preventing an increase in the number of components for performing user identification.

First Embodiment

Non-Burning Type Flavor Inhaler

Figure 2:
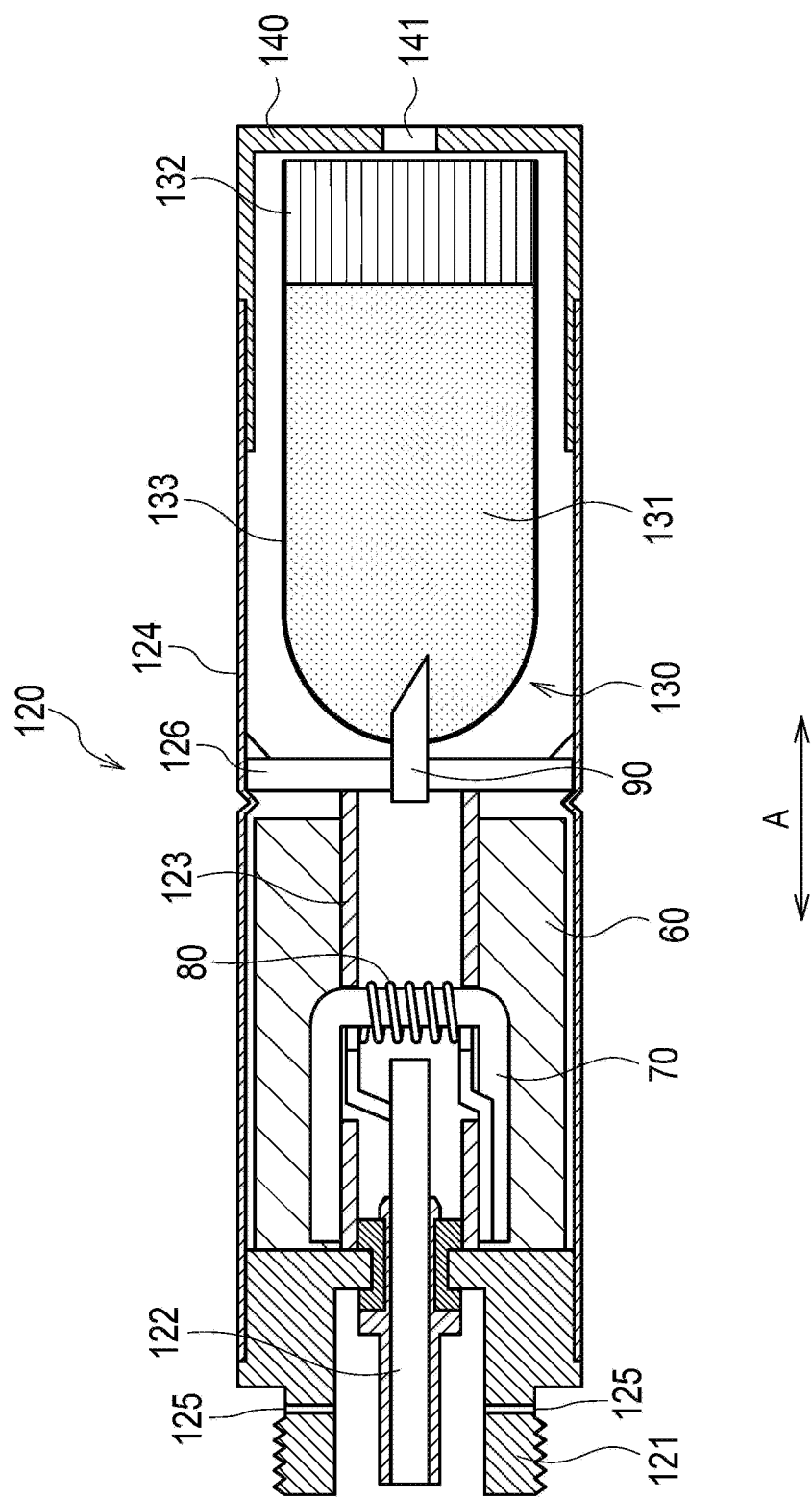
FIG. 2 is a diagram showing an atomization unit 120 according to the first embodiment.

A non-burning type flavor inhaler according to a first embodiment will be described, below. FIG. 1 is a diagram showing a non-burning type flavor inhaler 100 according to the first embodiment. FIG. 2 is a diagram showing an atomization unit 120 according to the first embodiment.

In the first embodiment, the non-burning type flavor inhaler 100 is a device for inhaling flavor without burning, and has a shape extending along a predetermined direction A from a non-mouthpiece side toward a mouthpiece side. In the first embodiment, the "mouthpiece side" may be considered synonymous with the "downstream" of the flow of the aerosol, and the "non-mouthpiece side" may be considered synonymous with the "upstream" of the flow of the aerosol.

As shown in FIG. 1, the non-burning type flavor inhaler 100 has an electrical unit 110 and an atomization unit 120. The electrical unit 110 has a female connector 111 at a site adjacent to the atomization unit 120, and the atomization unit 120 has a male connector 121 at a site adjacent to the electrical unit 110. The female connector 111 has a spiral groove extending along a direction perpendicular to the predetermined direction A, and the male connector 121 has a spiral projection extending along a direction perpendicular to the predetermined direction A. As a result of mating of the female connector 111 and the male connector 121, the atomization unit 120 and the electrical unit 110 are connected. The atomization unit 120 is configured in a removable manner with respect to the electrical unit 110.

The electrical unit 110 has a power source 10, a sensor 20, a push button 30, a light-emitting element 40, and a control circuit 50.

The power source 10 is, for example, a lithium ion battery. The power source 10 accumulates electric power necessary for the action of the non-burning type flavor inhaler 100. For example, the power source 10 accumulates electric power to be supplied to the sensor 20, the light-emitting element 40, and the control circuit 50. Further, the power source 10 accumulates electric power to be supplied to a heat source 80 described later.

The sensor 20 outputs a value (for example, a voltage value or a current value) that changes in accordance with the air inhaled from the non-mouthpiece side toward the mouthpiece side (that is, the puff action of the user). In the first embodiment, the sensor 20 has a capacitor, and outputs a value indicating electric capacitance of the capacitor that changes in accordance with the air inhaled from the non-mouthpiece side toward the mouthpiece side (that is, the puff action of the user). Here, the value output by the sensor 20 is a voltage value. The sensor 20 is, for example, a capacitor microphone sensor.

Figure 3:
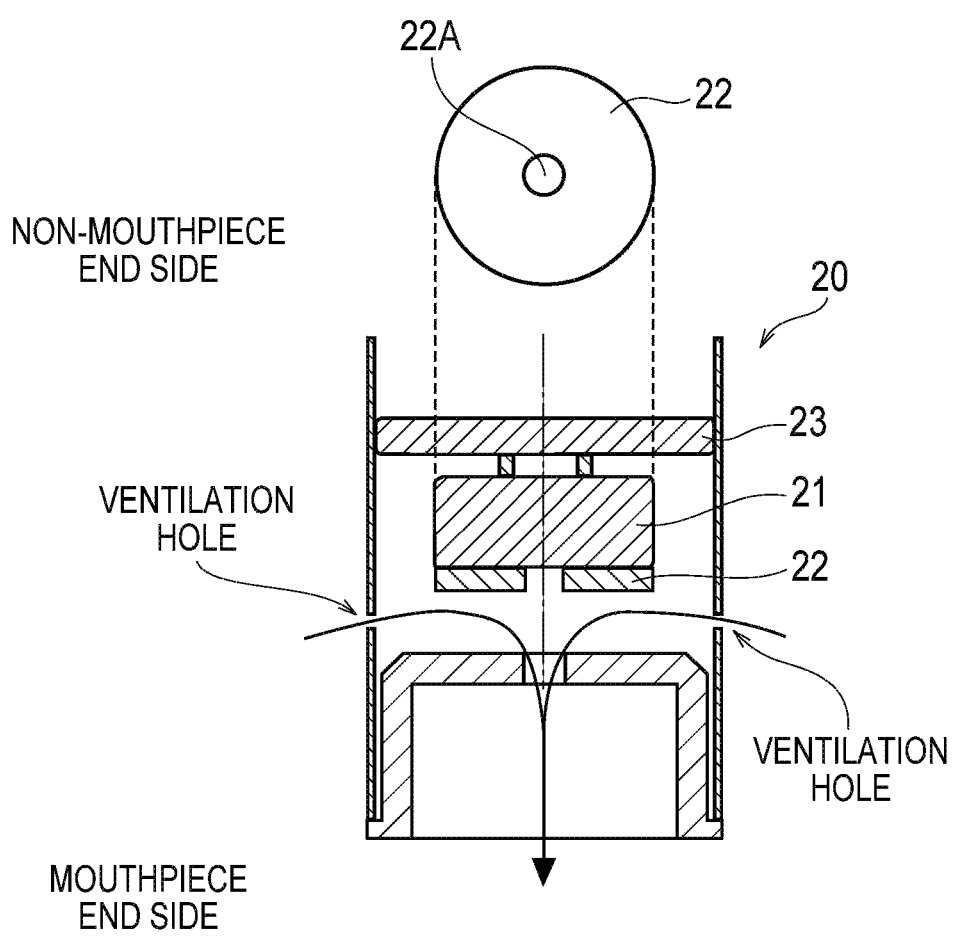
FIG. 3 is a diagram showing a sensor 20 according to the first embodiment.

Specifically, the sensor 20 has a sensor body 21, a cover 22, and a substrate 33, as shown in FIG. 3. The sensor body 21 is, for example, configured by a capacitor, and the electric capacitance of the sensor body 21 changes in accordance with the vibrations (pressure) generated by the air inhaled from an air lead-in hole 125 (that is, the air inhaled from the non-mouthpiece side toward the mouthpiece side). The cover 22 is provided at the mouthpiece side with respect to the sensor body 21, and has an opening 22A. By providing the cover 22 having the opening 22A, the electric capacitance of the sensor body 21 changes easily, and thereby the response characteristic of the sensor body 21 improves. The substrate 33 outputs a value (here, a voltage value) indicating the electric capacitance of the sensor body 21 (capacitor).

It is noted that in FIG. 3, the cover 22 covers only the mouthpiece side end of the sensor body 21, but the first embodiment is not limited thereto. For example, in addition to the mouthpiece side end of the sensor body 21, the cover 22 may cover the side surface of the sensor body 21. FIG. 3 illustrates a case in which the air lead-in hole 125 is provided at the mouthpiece side from the sensor 20, but the first embodiment is not limited thereto. For example, the air lead-in hole 125 may be provided at the non-mouthpiece side from the sensor 20.

Referring back to FIG. 1, the push button 30 is configured to be pushed from the outer side of the non-burning type flavor inhaler 100 toward the inner side. In the first embodiment, the push button 30 is provided at the non-mouthpiece end of the non-burning type flavor inhaler 100, and is configured to be pushed in a direction from the non-mouthpiece end toward the mouthpiece end (that is, the predetermined direction A). For example, when the push button 30 is pushed continuously over a predetermined number of times, the power source of the non-burning type flavor inhaler 100 is turned ON. It is noted that the power source of the non-burning type flavor inhaler 100 may be disconnected when a predetermined time period elapses while a puff action is not being performed from the time a puff action is performed.

The light-emitting element 40 is, for example, a light source such as an LED or an electric lamp. The light-emitting element 40 is provided on a side wall extending along a predetermined direction. The light-emitting element 40 is preferably provided on a side wall near the non-mouthpiece end. As a result, as compared to a case in which the light-emitting element is provided only on an end face of the non-mouthpiece end on an axial line of the predetermined direction A, the user is capable of visually recognizing, during the puff action, a light-emitting pattern of the light-emitting element 40 with ease. The light-emitting pattern of the light-emitting element 40 is a pattern by which a condition of the non-burning type flavor inhaler 100 is notified to the user.

The control circuit 50 controls the action of the non-burning type flavor inhaler 100. Specifically, the control circuit 50 controls the light-emitting pattern of the light-emitting element 40, and controls the power source output to the heat source 80.

As shown in FIG. 2, the atomization unit 120 has a holder 60, an absorber 70, the heat source 80, and a destruction portion 90. The atomization unit 120 has a capsule unit 130 and a mouthpiece unit 140. Here, the atomization unit 120 has the air lead-in hole 125 for taking in the outside air, an air flow path 122 communicated to the electrical unit 110 (sensor 20) via the male connector 121, and a ceramic 123 arranged in a cylindrical shape. The atomization unit 120 has a cylindrical outer wall 124 configured to form the outer shape of the atomization unit 120. The space enclosed by the ceramic 123 forms an air flow path. The ceramic 123, for example, includes alumina as the main constituent.

The holder 60 has a cylindrical shape, and holds an aerosol source configured to generate aerosol. The aerosol source is a liquid, such as glycerine or propylene glycol. The holder 60 is configured by a porous body in which the aerosol source has been immersed, for example. The porous body is, for example, a resin web.

It is noted that in the first embodiment, the above-described ceramic 123 is arranged on the inner side of the holder 60, and the volatilization of the aerosol source held by the holder 60 is thus restrained.

The absorber 70 is provided adjacent to the holder 60, and is configured by a substance that sucks up the aerosol source from the holder 60. The absorber 70 is, for example, configured by a glass fiber.

The heat source 80 heats the aerosol source without burning. That is, the heat source 80 is an example of an atomizer configured to atomize atomizes an aerosol source without burning. For example, the heat source 80 is a heating wire wound around the absorber 70. The heat source 80 heats the aerosol source that is sucked up by the absorber 70.

In the first embodiment, a heating type component configured to atomize the aerosol source by heating is illustrated as the heat source 80. However, as long as the atomizer has a function of atomizing the aerosol source, the atomizer may be an ultrasonic wave type component configured to atomize the aerosol source by an ultrasonic wave.

The destruction portion 90 is a member for destructing a part of a predetermined film 133 in a state in which the capsule unit 130 has been mounted. In the embodiment, the destruction portion 90 is held by a partition member 126 for separating the atomization unit 120 and the capsule unit 130. The partition member 126 is, for example, a polyacetal resin. The destruction portion 90 is, for example, a tubular hollow needle extending along the predetermined direction A. By piercing the tip of the hollow needle through the predetermined film 133, a part of the predetermined film 133 is destructed. Further, an air flow path that pneumatically communicates the atomization unit 120 and the capsule unit 130 is formed by the inner space of the hollow needle. Here, a mesh that has a roughness of an extent such that the raw material configuring a tobacco source 131 does not pass through is preferably provided inside the hollow needle. The roughness of the mesh is, for example, 80 mesh or above and 200 mesh or below.

In such a case, the depth of penetration of the hollow needle inside the capsule unit 130 is preferably 1.0 mm or more and 5.0 mm or less, and more preferably 2.0 mm or more and 3.0 mm or less. As a result, since there is no destruction of sites other than the desired site of the predetermined film 133, it is possible to prevent the desorption of the tobacco source 131 that is packed in the space partitioned by the predetermined film 133 and a filter 132. Further, since the detachment of the hollow needle from the concerned space is prevented, it is possible to favorably maintain the appropriate air flow path extending from the hollow needle to the filter 132.

In the vertical cross-section with respect to the predetermined direction A, the cross-sectional area of the vertical needle is preferably 2.0 mm$^2$ or more and 3.0 mm$^2$ or less. As a result, it is possible to prevent the dropping out of the tobacco source 131 from the capsule unit 130 when the hollow needle is pulled out.

The tip of the hollow needle preferably has an inclination of 30° or more and 45° or less with respect to the vertical direction to the predetermined direction A.

However, the embodiment is not restricted thereto, and the destruction portion 90 may be a site adjacent to the predetermined film 133 in a state in which the capsule unit 130 has been mounted. Apart of the predetermined film 133 may thus be destructed through the application of pressure to such a site by the user.

The capsule unit 130 is configured in a removable manner with respect to a main body unit. The capsule unit 130 has the tobacco source 131, the filter 132, and the predetermined film 133. Further, the tobacco source 131 is packed in the space partitioned by the predetermined film 133 and the filter 132. Here, the main body unit is a unit configured by sites other than the capsule unit 130. For example, the main body unit includes the above-described electrical unit 110, the holder 60, the absorber 70, and the heat source 80.

The tobacco source 131 is provided at the mouthpiece side from the holder 60 configured to hold the aerosol source, and generates a flavor that is inhaled by the user together with the aerosol generated from the aerosol source. Here, it must be noted that the tobacco source 131 is configured by a solid substance so as not to flow out from inside the space partitioned by the predetermined film 133 and the filter 132. As the tobacco source 131, it is possible to use shredded tobacco, a formed product obtained by forming the tobacco raw material in the shape of granules, and a formed product obtained by forming the tobacco raw material in the shape of a sheet. Flavorings, such as menthol, etc. may be added to the tobacco source 131.

It is noted that when the tobacco source 131 is configured by the tobacco raw material, the tobacco raw material is away from the heat source 80, and therefore, is it possible to inhale the flavor without heating the tobacco raw material. In other words, it must be noted that inhalation of unnecessary substances generated by heating of the tobacco raw material is controlled.

In the first embodiment, the amount of the tobacco source 131 that is packed in the space partitioned by the filter 132 and the predetermined film 133 is preferably 0.15 g/cc or more and 1.00 g/cc or less. The occupancy rate of the volume occupied by the tobacco source 131 in the space partitioned by the filter 132 and the predetermined film 133 is preferably 50% or more and 100% or less. It is noted that the capacity of the space partitioned by the filter 132 and the predetermined film 133 is preferably 0.6 mL or more and 1.5 mL or less. As a result, it is possible to store the tobacco source 131 to an extent at which the user is capable of sufficiently tasting the flavor while retaining the capsule unit 130 at an appropriate size.

The air-flow resistance (pressure loss) of the capsule unit 130 in the case when air is inhaled at a flow rate of 1050 cc/min. from the tip portion (destructed portion) of the capsule unit 130 up to the end of the filter 132 in a state when a part of the predetermined film 133 is destructed by the destruction portion 90, and the atomization unit 120 and the capsule unit 130 are communicated is preferably 10 mmAq or more and 100 mmAq or less, and more preferably 20 mmAq or more and 90 mmAq or less, as a whole. By setting the air-flow resistance of the tobacco source 131 within the above-described preferred range, the phenomenon of over-filtration of the aerosol by the tobacco source 131 is controlled, and thus, it is possible to efficiently supply the flavor to the user. It is noted that since 1 mmAq is equivalent to 9.80665 Pa, the above-described air-flow resistance is possible to be expressed in Pa as well.

The filter 132 is adjacent to the mouthpiece side with respect to the tobacco source 131, and is configured by a substance having air permeability. The filter 132 is preferably, for example, an acetate filter. The filter 132 preferably has a roughness of an extent such that the raw material configuring the tobacco source 131 does not pass through.

The air-flow resistance of the filter 132 is preferably 5 mmAq or more and 20 mmAq or less. As a result, it is possible to efficiently let the aerosol pass through while efficiently adsorbing the vapor component generated from the tobacco source 131, and thus, it is possible to supply an appropriate flavor to the user. Further, it is possible to offer the user the appropriate sense of resistance to air.

The ratio (mass ratio) of the mass of the tobacco source 131 and the mass of the filter 132 is preferably in the range of 3:1 to 20:1, and more preferably in the range of 4:1 to 6:1.

The predetermined film 133 is integrally formed with the filter 132, and is configured by a member that does not have air permeability. Of the outer surface of the tobacco source 131, the predetermined film 133 covers a portion excluding the portion adjacent to the filter 132. The predetermined film 133 includes at least one compound selected from a group configured by gelatin, polypropylene, and polyethylene terephthalate. Gelatin, polypropylene, polyethylene, and polyethylene terephthalate do not have air permeability, and are suitable for the formation of a thin film. Further, gelatin, polypropylene, polyethylene, and polyethylene terephthalate are able to acquire sufficient durability against the moisture contained in the tobacco source 131. Polypropylene, polyethylene, and polyethylene terephthalate particularly have excellent water resistance. In addition, gelatin, polypropylene, and polyethylene have resistance to bases, and hence not tend to be degraded by the basic component even if the tobacco source 131 has a basic component.

The predetermined film 133 preferably has a film thickness of 0.1 μm or more and 0.3 μm or less. As a result, it is possible to easily destruct a part of the predetermined film 133 while maintaining the function of protecting the tobacco source 131 by the predetermined film 133.

As described above, the predetermined film 133 is integrally formed with the filter 132, however, the predetermined film 133, for example, is affixed on to the filter 132 by glue, or the like. Alternatively, the outer shape of the predetermined film 133 may be set to be smaller than the outer shape of the filter 132 in the vertical direction to the predetermined direction A so as to pack the filter 132 within the predetermined film 133, and fit the filter 132 within the predetermined film 133 by the restoring force of the filter 132. Else, an engagement portion for engaging the predetermined film 133 may be provided in the filter 132.

Here, although the shape of the predetermined film 133 is not particularly restricted, the predetermined film 133 preferably has a concave shape in the vertical cross-section with respect to the predetermined direction A. In such a case, after packing the tobacco source 131 inside the predetermined film 133 having a concave shape, the opening of the predetermined film 133 in which the tobacco source 131 is packed is closed by the filter 132.

When the predetermined film 133 has a concave shape in the vertical cross-section with respect to the predetermined direction A, of the cross-sectional area of the space enclosed by the predetermined film 133, the maximum cross-sectional area (that is, the cross-sectional area of the opening in which the filter 132 is fitted) is preferably 25 mm$^2$ or more and 80 mm$^2$ or less, and more preferably 25 mm$^2$ or more and 55 mm$^2$ or less. In such a case, the cross-sectional area of the filter 132 in the vertical cross-section with respect to the predetermined direction A is preferably 25 mm$^2$ or more and 55 mm$^2$ or less. The thickness of the filter 132 in the predetermined direction A is preferably 3.0 mm or more and 7.0 mm or less.

The mouthpiece unit 140 has a mouthpiece hole 141. The mouthpiece hole 141 is an opening configured to expose the filter 132. By inhaling aerosol from the mouthpiece hole 141, the user inhales the flavor together with the aerosol.

In the first embodiment, the mouthpiece unit 140 is configured in a removable manner with respect to the outer wall 124 of the atomization unit 120. For example, the mouthpiece unit 140 has a cup shape that is configured to fit in the inner surface of the outer wall 124. However, the embodiment is not limited thereto. The mouthpiece unit 140 may be attached to the outer wall 124 in a rotatable manner with the help of a hinge, etc.

In the first embodiment, the mouthpiece unit 140 is provided as a separate part from the capsule unit 130. That is, the mouthpiece unit 140 configures a part of the main body unit. However, the embodiment is not limited thereto. The mouthpiece unit 140 may be integrally provided with the capsule unit 130. In such a case, it must be noted that the mouthpiece unit 140 configures a part of the capsule unit 130.

As described above, in the first embodiment, the non-burning type flavor inhaler 100 has the outer wall 124 (housing) of the atomization unit 120 having the air flow path 122 that continues from the air lead-in hole 125 (inlet) to the mouthpiece hole 141 (outlet). In the first embodiment, the air flow path 122 is configured by the atomization unit 120, but the aspect of the air flow path 122 is not limited thereto. The air flow path 122 may be configured by both a housing of the electrical unit 110, and a housing of the atomization unit 120.

(Control Circuit)

Figure 4:
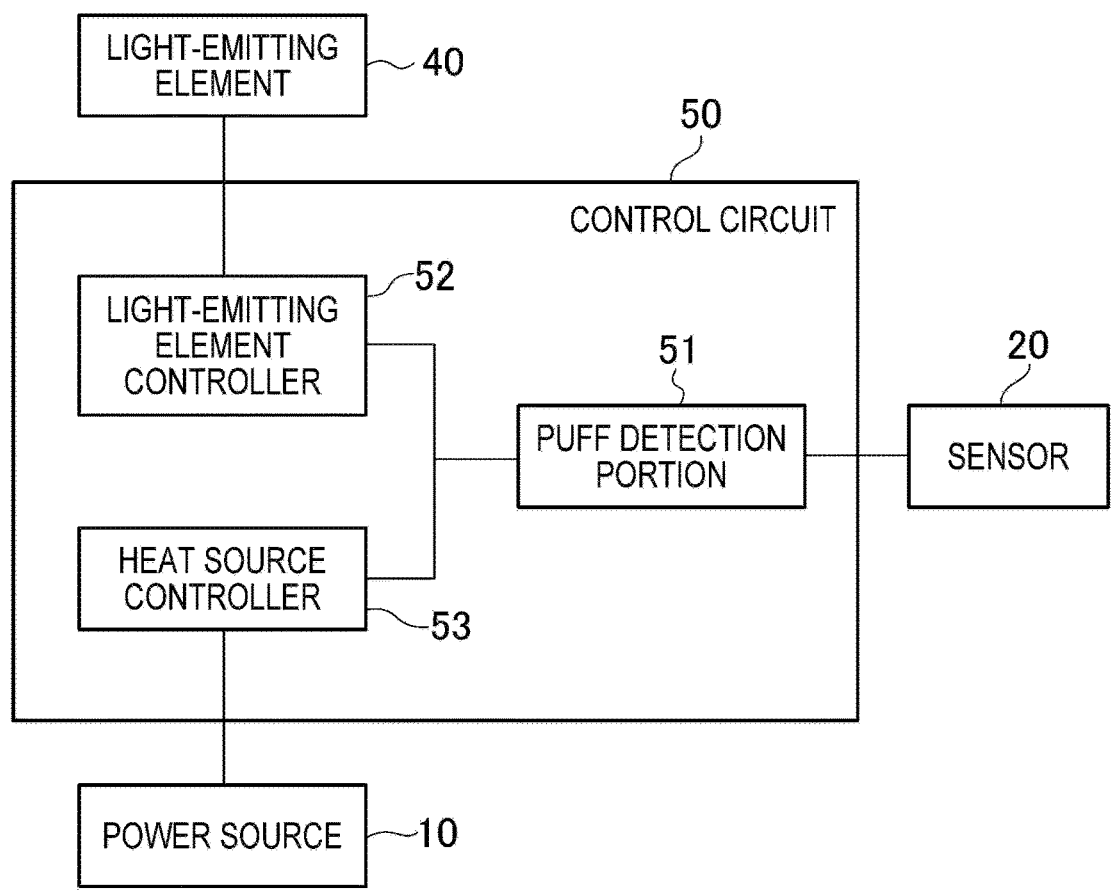
FIG. 4 is a block diagram showing a control circuit 50 according to the first embodiment.

A control circuit according to the first embodiment will be described, below. FIG. 4 is a block diagram showing a control circuit 50 according to the first embodiment.

As shown in FIG. 4, the control circuit 50 has a puff detection portion 51, a light-emitting element controller 52, and a heat source controller 53.

The puff detection portion 51 is connected to a sensor 20 configured to output a value that changes in accordance with the air inhaled from the non-mouthpiece side toward the mouthpiece side. The puff detection portion 51 detects the puffing state, on the basis of the detection result (for example, the negative pressure in the non-burning type flavor inhaler 100) of the sensor 20. In particular, the puff detection portion 51 detects a puffing state in which aerosol is inhaled (puff duration), and a non-puffing state in which aerosol is not inhaled (non-puff duration). As a result, the puff detection portion 51 is capable of specifying the number of times of the puff action of inhaling aerosol. Further, the puff detection portion 51 is also capable of detecting a required time of a one-time puff action of inhaling aerosol.

In the first embodiment, the puff detection portion 51 detects, on the basis of an inclination configured by two or more response values derived from an output value that is output from the sensor 20, the start or the end of the puff duration. Here, the response value is an output value itself that is output from the sensor 20, and the output value is a voltage value indicating the electric capacitance of the capacitor.

Specifically, the puff detection portion 51 detects the start or the end of the puff duration, when an inclination configured by two or more output values that are output from the sensor 20 has a predetermined sign (here, negative), and an absolute value of the inclination having the predetermined sign (here, negative) is larger than a predetermined value. In other words, the puff detection portion 51 detects the start of the puff duration when the above-described condition is satisfied before the detection of the start of the puff duration. On the other hand, the puff detection portion 51 detects the end of the puff duration when the above-described condition is satisfied after the detection of the start of the puff duration.

Here, a condition (predetermined value) used for the start of the puff duration may either be the same or different from a condition (predetermined value) used for the end of the puff duration. Further, the determination of the end of the puff duration is preferably performed after the lapse of a predetermined time period (for example, 200 msec to 500 msec) from the detection of the start of the puff duration. As a result, a situation is prevented where the end of the puff duration is erroneously detected immediately after the detection of the start of the puff duration.

Figure 5:
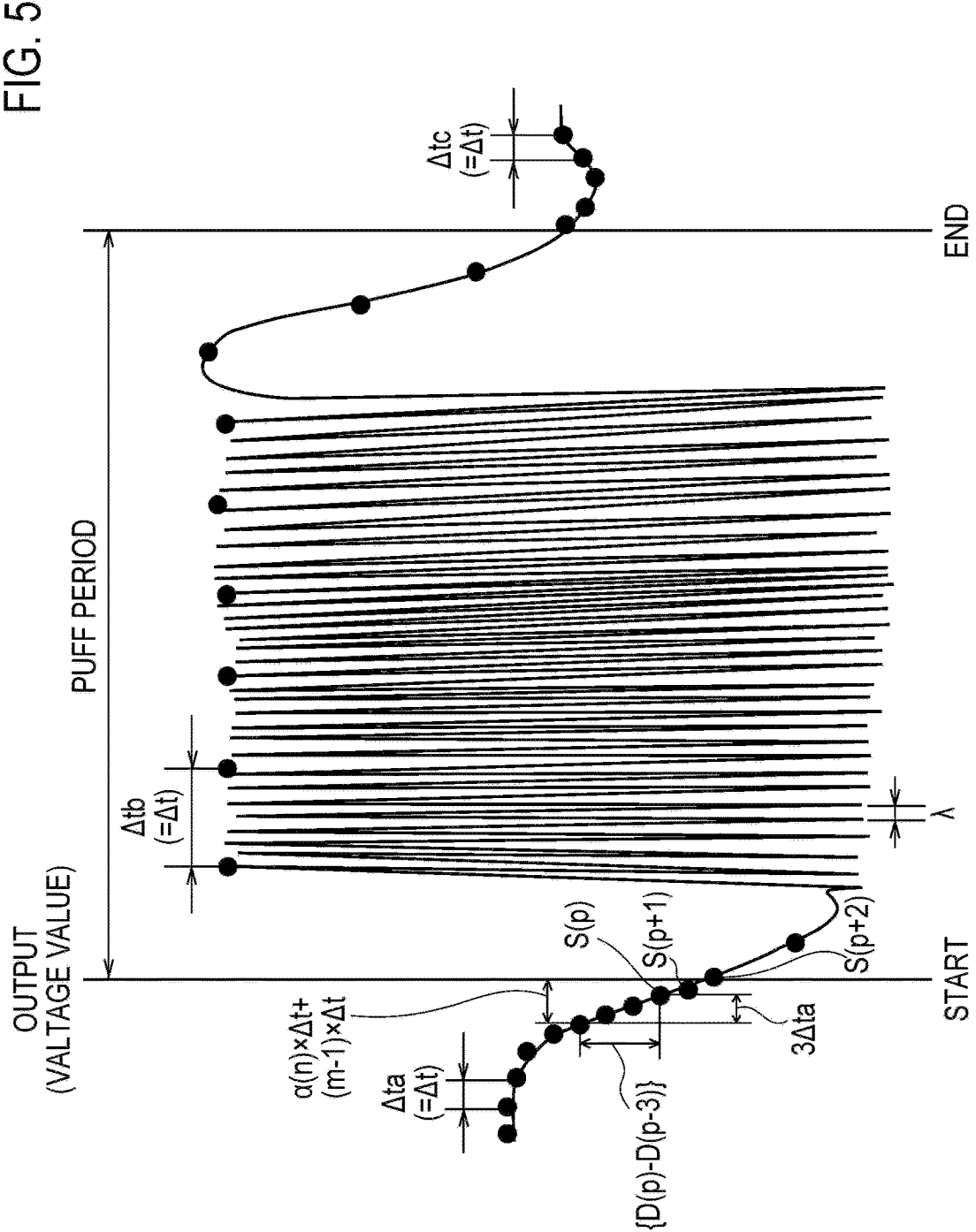
FIG. 5 is a diagram for describing a detection of a puff duration according to the first embodiment.

In particular, as shown in FIG. 5, the puff detection portion 51 monitors the output value that is output from the sensor 20 in a sampling cycle ($\Delta t$). In FIG. 5, it must be noted that a voltage value is illustrated as an output value that is output from the sensor 20. A sampling cycle ($\Delta ta$) in which the output value that is output from the sensor 20 is monitored before the detection of the start of the puff duration is shorter than a sampling cycle ($\Delta tb$) in which the output value that is output from the sensor 20 is monitored after the detection of the start of the puff duration. A sampling cycle ($\Delta tc$) in which the output value that is output from the sensor 20 is monitored after the detection of the end of the puff duration is shorter than the sampling cycle ($\Delta tb$) in which the output value that is output from the sensor 20 is monitored before the detection of the end of the puff duration.

It is noted that the sampling cycle ($\Delta ta$) in which the output value that is output from the sensor 20 is monitored before the detection of the start of the puff duration is similar to the sampling cycle ($\Delta tc$) in which the output value that is output from the sensor 20 is monitored after the detection of the end of the puff duration. Further, the sampling cycle ($\Delta tb$) in which the output value that is output from the sensor 20 is monitored after the detection of the start of the puff duration is similar to the sampling cycle ($\Delta tb$) in which the output value that is output from the sensor 20 is monitored before the detection of the end of the puff duration. In other words, the sampling cycle ($\Delta ta$ or $\Delta tc$) in which the output value that is output from the sensor 20 is monitored outside the puff duration is shorter than the sampling cycle ($\Delta tb$) in which the output value that is output from the sensor 20 is monitored within the puff duration. The sampling cycle ($\Delta ta$ or $\Delta tc$) in which the output value that is output from the sensor 20 is monitored outside the puff duration is, for example, 1 msec, and the sampling cycle ($\Delta tb$) in which the output value that is output from the sensor 20 is monitored within the puff duration is, for example, 10 msec.

Hereinafter, each symbol represents the below-mentioned contents. $\Delta t$ represents a cycle in which the output value that is output from the sensor 20 is monitored, D(n) represents the output value that is output from the sensor 20 in time t(n), $\alpha$(n) represents a positive integer, and S(n) represents an inclination configured by the output value that is output from the sensor 20 in time t(n). It is noted that n represents the calculation frequency of S(n). Further, $\alpha$(n) may be a constant value (for example, 3), or may change every time S(n) is calculated.

Under such a prerequisite, the puff detection portion 51 may calculate, by $S(n)=\{D(n)-D(n-\alpha(n)\times\Delta t)\}/(\alpha(n)\times\Delta t)$, the inclination configured by the output value that is output from the sensor 20. It must be noted that "$D(n-\alpha(n)\times\Delta t)$" represents the output value that is monitored only "$\alpha(n)\times\Delta t$" time before the time t(n).

In such a case, the puff detection portion 51 detects the start of the puff duration, when, for consecutive m times (m is an integer value of 2 or more) of S(n), a condition is satisfied before the detection of the start of the puff duration, in which all S(n)s are the value of a predetermined sign (here, negative), and the absolute value of all S(n)s is larger than a first value that is described later. Here, it must be noted that the sampling cycle ($\Delta t$) used when detecting the start of the puff duration is $\Delta ta$ (or $\Delta tc$). On the other hand, the puff detection portion 51 detects the end of the puff duration, when, for consecutive m times of S(n), a condition is satisfied after the detection of the start of the puff duration, in which all S(n)s are the value of a predetermined sign (here, negative), and the absolute value of all S(n)s is larger than the first value. Here, it must be noted that the sampling cycle ($\Delta t$) used when detecting the end of the puff duration is $\Delta tb$ (>$\Delta ta$ or $\Delta tc$).

For example, a case of detection of the start of the puff duration when $\alpha(n)=3$ and m=3 will be described while referencing FIG. 5. In such a case, since all of S(p), S(p+1), and S(p+2) have a negative value, and the absolute values of all of S(p), S(p+1), and S(p+2) are larger than the first value, the start of the puff duration is detected in time p+2. It is noted that as a calculation method of S(n), if an explanation is provided using time p as an example, then S(p) is calculated by $S(p)=\{D(p)-D(p-3)/3\Delta t\}$.

It is noted that the first value is a predetermined value that is decided beforehand, and may be set appropriately depending on the type, etc. of the sensor 20. Further, a cycle by which the puff detection portion 51 calculates S(n) may be same as the sampling cycle ($\Delta t$), or may be different from the sampling cycle ($\Delta t$). It is noted that the cycle by which the puff detection portion 51 calculates S(n) is preferably an integral multiple of the sampling cycle ($\Delta t$).

It is noted that the sampling cycle ($\Delta t$) and a calculation cycle of S(n) are possible to be set appropriately. While it is preferable that the sampling cycle ($\Delta t$) and the calculation cycle of S(n) are synchronous, the sampling cycle ($\Delta t$) and the calculation cycle of S(n) may not necessarily be synchronous. Further, a cycle in which the sensor 20 outputs the output value is also possible to be set appropriately. In addition, the sensor 20 may repeatedly turn ON/OFF in synchronization with the sampling cycle ($\Delta t$) and the calculation cycle of S(n), or may be ON at all times.

In the first embodiment, a sampling cycle (for example, 5 msec.) of the output value that is referenced during the determination of the start or end of the puff duration is preferably longer than a predetermined time. Specifically, the sampling cycle of the output value that is referenced when determining the start or end of the puff duration is represented by $\alpha(n)\times\Delta t+(m-1)\times\Delta t$, as shown in FIG. 5. The predetermined time period is preferably longer than ½ of the average value of a wavelength (λ shown in FIG. 5) of a frequency of a waveform derived from a continuous approximation function, where the continuous approximation function is derived, under the prerequisite that the output value that varies in the puff duration is discretely acquired on the time axis, from the plot of the output value acquired discretely. Thus, by setting a lower limit for the sampling cycle of the output value that is referenced when determining the start or the end of the puff duration, the fact is prevented that the above-described conditions are accidently satisfied before the detection of the start of puff duration by an event that is different from the puff action of the user (for example, the vibration of human voice, etc.), and the accuracy of detection of the start of the puff duration is improved. Further, even after the detection of the start of the puff duration, the fact is prevented that the above-described conditions are accidently satisfied before the user actually ends the puff action, and the accuracy of detection of the end of the puff duration is improved.

In the first embodiment, the puff detection portion 51 preferably detects the start or the end of the puff duration, when, for one time of the consecutive m times of S(n), a condition is satisfied in which an absolute value of S(n) is smaller than a second value. The second value is preferably a value that is sufficiently larger than the first value, and that is an average value of an inclination (absolute value) configured by two or more output values that vary in a puff duration. In other words, the puff detection portion 51 does not detect the start or the end of the puff duration, when, for all of the consecutive m times of S(n)s, S(n) is a value of a predetermined sign (here, negative), and an absolute value of S(n) is equal to or larger than the second value. On the other hand, the puff detection portion 51 detects the start or the end of the puff duration, when, for consecutive m times of S(n), a condition is satisfied in which all S(n)s are larger than the first value, and a condition is also satisfied in which the absolute value of at least one time of S(n) is smaller than the second value. As a result, even when the electric capacitance of the sensor 20 changes rapidly due to an event that is different from the puff action, the erroneous detection of the start or the end of the puff duration is controlled. An event that is different from the puff action implies, for example, an event where in a case in which the non-burning type flavor inhaler 100 is kept on a table, the electric capacitance of the sensor 20 changes due to the vibrations on the table, and an event where rather than inhaling, the user performs blowing from the mouthpiece of the non-burning type flavor inhaler 100.

In the first embodiment, the sampling cycle of the output value that is referenced when determining the start or end of the puff duration is $\alpha(n) \times \Delta t + (m-1) \times \Delta t$. That is, the sampling cycles of the output values that are referenced during the calculation of consecutive two times of S(n) of m times of S(n) partially overlap each other, and $\alpha(n)$ is 2 or more. As a result, as compared to a case in which the sampling cycles of the output values that are referenced during the calculation of consecutive two times of S(n) do not overlap, that is, a case in which the sampling cycle of the output value that is referenced when determining the start or the end of the puff duration is $\alpha(n) \times \Delta t \times m$, the sampling cycle $(\alpha(n) \times \Delta t + (m-1) \times \Delta t)$ of the output value that is referenced when determining the start or the end of the puff duration is shorter, because of which it is possible to quickly detect the start of the puff duration, and thus, the detection accuracy of the start of the puff duration is improved. In addition, as compared to a case in which $\alpha(n)$ is 1, a slight variation in the output value is not detected as the start of the puff duration, and therefore, it is possible to prevent the erroneous detection of the puff duration.

The light-emitting element controller 52 is connected to the light-emitting element 40 and the puff detection portion 51, and controls the light-emitting element 40. Specifically, the light-emitting element controller 52 controls the light-emitting element 40 according to a first light-emitting mode, in the puffing state in which aerosol is inhaled. On the other hand, the light-emitting element controller 52 controls the light-emitting element 40 according to a second light-emitting mode that is different from the first light-emitting mode, in the non-puffing state in which aerosol is not inhaled.

Here, the light-emitting mode is defined according to a combination of parameters such as the amount of light of the light-emitting element 40, the number of the light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

In the first embodiment, the second light-emitting mode changes in accordance with the number of times of the puff action of inhaling aerosol. The first light-emitting mode may change in accordance with the number of times of the puff action of inhaling aerosol, or may be fixed regardless of the number of times of the puff action of inhaling aerosol.

For example, the first light-emitting mode is a mode in which a red-colored light-emitting element 40 is lit up in order to imitate the sense of use of a regular cigarette in which aerosol is generated in association with burning. The first light-emitting mode is preferably a mode in which the light-emitting element 40 is continuously lit up. Alternatively, the first light-emitting mode may be a mode in which lighting up of the light-emitting element 40 and lighting out of the light-emitting element 40 are repeated in a first cycle.

For example, the second light-emitting mode is a mode in which a blue-colored light-emitting element 40 is lit up in order to notify the user that the aerosol source is not heated up. The second light-emitting mode may be a mode in which lighting up of the light-emitting element 40 and lighting out of the light-emitting element 40 are repeated in a second cycle that is longer than the first cycle.

As described above, the second light-emitting mode changes in accordance with the number of times of the puff action of inhaling aerosol.

For example, the second light-emitting mode may be a mode in which the number of light-emitting elements 40 that are to be controlled increases with an increase in the number of times of the puff action. For example, the light-emitting element controller 52 controls one light-emitting element 40 by the second light-emitting mode in the first puff action, and controls two light-emitting elements 40 by the second light-emitting mode in the second puff action. Alternatively, the light-emitting element controller 52 controls n number of light-emitting elements 40 by the second light-emitting mode in the first puff action, and controls n−1 number of light-emitting elements 40 by the second light-emitting mode in the second puff action.

Alternatively, the second light-emitting mode may be a mode in which the amount of light of the light-emitting element 40 either increases or decreases with an increase in the number of times of the puff action. Else, the second light-emitting mode may be a mode in which the color of the light-emitting element 40 changes with an increase in the number of times of the puff action.

It is noted that even when the first light-emitting mode changes in accordance with the number of times of the puff action, the change in the first light-emitting mode is basically the same concept as the change in the second light-emitting mode.

In the first embodiment, when the number of times of the puff action of inhaling the aerosol reaches a predetermined number of times (for example, eight times), the light-emitting element controller 52 ends the control complying with the first light-emitting mode and the second light-emitting mode, and controls the light-emitting element 40 with an end light-emitting mode.

The end light-emitting mode is preferably different from the first light-emitting mode and the second light-emitting mode as long as the end light-emitting mode is a mode for notifying the user that it is time to end the puff action. For example, the end light-emitting mode is a mode in which the amount of light of the light-emitting element 40 is smaller than the first light-emitting mode and the second light-emitting mode, and the amount of light of the light-emitting element 40 reduces over time.

The heat source controller 53 is connected to the power source 10, and controls the power source output (here, the amount of electric power) from the power source 10 to the heat source 80 (atomizer). It is noted that the amount of electric power is the result of multiplication of time and electric power (voltage or current), and is a value that is controlled by time and electric power. For example, the heat source controller 53 controls the voltage applied to the heat source 80 from the power source 10 by controlling the DC-DC converter, etc. that is arranged together with the power source 10.

Here, in a case where a voltage is applied continuously to the heat source 80 (atomizer), the amount of power source output (integrated value) is defined by the value of the voltage applied to the heat source 80 (atomizer) and the time for which the supply of the power source output continues. On the other hand, in a case (pulse control) where a voltage is applied intermittently to the heat source 80 (atomizer), the amount of power source output (integrated value) is defined by the value of the voltage applied to the heat source 80 (atomizer), the pulse width, the pulse interval, and the time for which the supply of the power source output continues.

It must be noted that in the first embodiment, the heat source controller 53 starts the supply of the power source output from the power source 10 to the heat source 80 in the puff duration during which a puff action is performed, and the heat source controller 53 stops the supply of the power source output from the power source 10 to the heat source 80 in the non-puff duration during which a puff action is not performed.

Firstly, the heat source controller 53 gradually increases the power source output to the heat source 80 from the standard power source output in association with an increase in the number of times of the puff action of inhaling the aerosol. As a result, it becomes possible to imitate the sense of use of a regular cigarette configured to generate aerosol in association with burning.

Here, the heat source controller 53 may control the power source 10 in such a way that when a puff action is performed after the number of times of the puff action exceeds the predetermined number of times, a power source output that is smaller than the standard power source output is supplied to the heat source 80. As a result, even if it is time to end the puff action, the user is capable of inhaling just a small amount of the aerosol, by which it is possible to increase the level of satisfaction of the user.

When a predetermined time period has elapsed after the number of times of the puff action exceeds a predetermined number of times, the heat source controller 53 turns OFF the power source of the non-burning type flavor inhaler 100. As a result, the waste of electric power of the non-burning type flavor inhaler 100 due to forgetting to turn off the power source of the non-burning type flavor inhaler 100 is controlled.

Here, the heat source controller 53 may combine the above-described actions to supply a power source output that is smaller than the standard power source output to the heat source 80 after the number of times of the puff action exceeds a predetermined number of times, and to turn OFF the power source of the non-burning type flavor inhaler 100 after the number of times of the puff action exceeds the predetermined number of times as well as when the predetermined time has elapsed.

The heat source controller 53 preferably increases the gradient of the power source output to the heat source 80 with an increase in the number of times of the puff action of inhaling the aerosol. Here, the gradient of the power source output is defined by the number of times of the puff action during which a fixed power source output is maintained, and the increment by which the power source output increases. That is, there is a reduction, with an increase in the number of times of the puff action, in the number of times of the puff action during which a fixed power source output is maintained. Alternatively, there is an increase, with an increase in the number of times of the puff action, in the increment by which the power source output increases. Alternatively, with an increase in the number of times of the puff action, there is a reduction in the number of times of the puff action during which a fixed power source output is maintained, and an increase in the increment by which the power source output increases.

In addition, the heat source controller 53 may control a first mode in which a first standard power source output is used as the standard power source output, and a second mode in which a second standard power source output that is greater than the first standard power source output is used as the standard power source output. Three or more stages of the standard power source output may be prepared as the standard power source output. In such a case, the switching of the standard power source output may be performed by an operation of the push button 30. For example, the first mode may be applied by pushing the push button 30 one time, and the second mode may be applied by pushing the push button 30 twice. Further, the push button 30 may be substituted by a touch sensor. The power source of the non-burning type flavor inhaler 100 may also be turned ON by performing the above-described operations. That is, turning ON of the power source and switching of the standard power source output may be performed by a single action by operating the push button 30. However, the action of turning ON the power source by operating the push button 30 may be separate from the action of switching the standard power source output.

Secondly, the heat source controller 53 controls a standard mode that must be applied to a user for whom the required time of a one-time puff action for inhaling aerosol is within the standard required time duration, and a shortened mode that must be applied to a user for whom the required time of a one-time puff action for inhaling aerosol is shorter than the standard required time duration. Here, the standard required time duration implies a time duration when the balance of the amount of supply of the aerosol (amount of TPM (Total Particulate Matter)) is particularly good.

Specifically, in a one-time puff action of the standard mode, the heat source controller 53 controls the power source 10 such that the standard power source output is supplied to the heat source 80 for the duration until a first time period elapses, and controls the power source 10 such that a power source output that is smaller than the standard power source output is supplied to the heat source 80 for the duration after the first time period has elapsed. It is noted that for the duration after the first time period has elapsed, the heat source controller 53 may immediately set the power source output to the heat source 80 to zero, or may reduce the power source output to the heat source 80 over time.

Here, the first time period is preferably same as the end timing of the above-described standard required time duration. However, the first time period may be longer than the end timing of the standard required time duration within a range in which the balance of the amount of supply of the aerosol (the TPM amount) is permitted.

On the other hand, in a one-time puff action of the shortened mode, the heat source controller 53 controls the power source 10 such that a first power source output that is greater than the standard power source output is supplied to the heat source 80 for the duration until a second time period elapses, and controls the power source 10 such that a second power source output that is smaller than the first power source output is supplied to the heat source 80 for the duration until a third time period after the second time period elapses, and also controls the power source 10 such that a power source output that is smaller than the second power source output is supplied to the heat source 80 for the duration after the third time period has elapsed. It is noted that for the duration after the third time period has elapsed, the heat source controller 53 may immediately set the power source output to the heat source 80 to zero, or may reduce the power source output to the heat source 80 over time.

Here, the second time period is preferably shorter than the start timing of the above-described standard required time duration. However, the second time period may be included in the standard required time duration, or may be longer than the end timing of the standard required time duration. The third time period is preferably same as the end timing of the above-described standard required time duration. However, the third time period may be longer than the end timing of the standard required time duration within a range in which the balance of the amount of supply of the aerosol (the TPM amount) is permitted. Further, the second power source output that is smaller than the first power source output may be the same as the above-described standard power source output. However, the second power source output may be greater than the standard power source output, or may be smaller than the standard power source output.

It is noted that as described above, the heat source controller 53 gradually increases the power source output to the heat source 80 from the standard power source output with an increase in the number of times of the puff action. In other words, it must be noted that the standard power source output in a one-time puff action increases an increase in the number of times of the puff action.

The heat source controller 53 may set the standard mode or the shortened mode depending on the learning of the puff action by the user. In particular, when the required time of a one-time puff action that is acquired by learning is within the standard required time duration, the heat source controller 53 sets the standard mode. When the required time of a one-time puff action that is acquired by learning is shorter than the standard required time duration, the heat source controller 53 sets the shortened mode.

In the first embodiment, the atomization unit 120 is removable with respect to the electrical unit 110. Further, the capsule unit 130 is removable with respect to the main body unit including the electrical unit 110. In other words, it is possible to reuse the electrical unit 110 over a plurality of times of puff action series. A puff action series is a series of actions in which the puff action is repeated a predetermined number of times. Therefore, by learning the required time of a one-time puff action in the first puff action series, the standard mode or the shortened mode may be set in the second puff action series or thereafter. Alternatively, by learning the required time of a one-time puff action in the first n-time puff actions in a one-time puff action series, the standard mode or the shortened mode may be set for the n+1 (or, n+2)th puff action or thereafter.

Alternatively, the heat source controller 53 may set the standard mode or the shortened mode depending on the operation by the user. In such a case, a switch for switching the standard mode and the shortened mode is provided in the non-burning type flavor inhaler 100. It is noted that the switching of the standard mode and the shortened mode may be permitted in a one-time puff action series. Alternatively, the mode that is set initially may be applied in a fixed manner without permitting the switching of the standard mode and the shortened mode in a one-time puff action series.

(Light-Emitting Mode)

An example of a light-emitting mode according to the first embodiment will be described, below. FIG. 6 and FIG. 7 are diagrams showing an example of the light emitting mode according to the first embodiment. FIG. 6 and FIG. 7 illustrate a case in which a user must end a puff action series, in principle, when the number of times of the puff action reaches eight times (a predetermined number of times).

Firstly, a first example of the light-emitting mode will be described with reference to FIG. 6. As shown in FIG. 6, a first light-emitting pattern in the puffing state is fixed regardless of the number of times of the puff action. On the other hand, a second light-emitting pattern in the non-puffing state changes in accordance with the number of times of the puff action.

For example, as shown in FIG. 6, in a non-puffing state #1 to a non-puffing state #4, a light-emitting mode #2-1 is used as the second light-emitting mode. In a non-puffing state #5 to a non-puffing state #7, a light-emitting mode #2-2 is used as the second light-emitting mode. In a non-puffing state #8, a light-emitting mode #2-3 is used as the second light-emitting mode. It is noted that in the ninth non-puffing state and thereafter, the above-described end light-emitting mode is used.

On the other hand, in a puffing state #1 to a puffing state #8, a light-emitting mode #1 is used as the first light-emitting mode. Even in the ninth puffing state and thereafter, the light-emitting mode #1 may be used as the first light-emitting mode, or a light-emitting mode different from the first light-emitting mode and the second light-emitting mode may be used in order to indicate that the puff is in excess of eight times (predetermined number of times).

The light-emitting mode #1, the light-emitting mode #2-1, the light-emitting mode #2-2, the light-emitting mode #2-3, and the end light-emitting mode are different light-emitting modes to each other. As described above, the light-emitting mode is defined according to a combination of parameters such as the amount of light of the light-emitting element 40, the number of the light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

For example, the light-emitting mode #1 is preferably a light-emitting mode that offers an image of burning in order to imitate the sense of use of a regular cigarette in which aerosol is generated in association with burning. The light-emitting mode #2-1 is a light-emitting mode that offers an image of an initial stage of the puff action series, the light-emitting mode #2-2 is a light-emitting mode that offers an image of a middle stage of the puff action series, and the light-emitting mode #2-3 is a light-emitting mode that offers an image of an end stage of the puff action series. The end light-emitting mode is preferably a mode for notifying the user that it is time to end the puff action.

Secondly, the first example of the light-emitting mode will be described with reference to FIG. 7. As shown in FIG. 7, both the first light-emitting pattern in the puffing state and the second light-emitting pattern in the non-puffing state change in accordance with the number of times of the puff action.

For example, as shown in FIG. 7, in the non-puffing state, the light-emitting mode #2-1, the light-emitting mode #2-2, and the light-emitting mode #2-3 are used as the second light-emitting mode, in a similar manner of the case shown in FIG. 6.

On the other hand, in the puffing state #1 to the puffing state #4, a light-emitting mode #1-1 is used as the first light-emitting mode. In a puffing state #5 to a puffing state #7, a light-emitting mode #1-2 is used as the first light-emitting mode. In a puffing state #8, a light-emitting mode #1-3 is used as the first light-emitting mode. It is noted that in the ninth puffing state and thereafter, a light-emitting mode #1-4 is used.

It is preferable that the light-emitting mode #1-1 is a light-emitting mode that offers an image of an initial stage of the puff action series, the light-emitting mode #1-2 is a light-emitting mode that offers an image of a middle stage of the puff action series, and the light-emitting mode #1-3 is a light-emitting mode that offers an image of an end stage of the puff action series. It is noted that, similarly to the end light-emitting mode, the light-emitting mode #1-4 is preferably a mode for notifying the user that it is time to end the puff action.

As shown in FIG. 6 and FIG. 7, the first embodiment illustrates a case in which the light-emitting mode in the non-puffing state #1 (that is, the non-puffing state immediately after turning ON the power source of the non-burning type flavor inhaler 100) is the second light-emitting mode (light-emitting mode #2-1). However, the embodiment is not limited thereto. The light-emitting mode in the non-puffing state #1 may be a start light-emitting mode that is different from the second light-emitting mode. The start light-emitting mode is preferably a mode for notifying the user that preparations have been made to start the puff action.

(Power Control in Puff Action Series)

Figure 9:
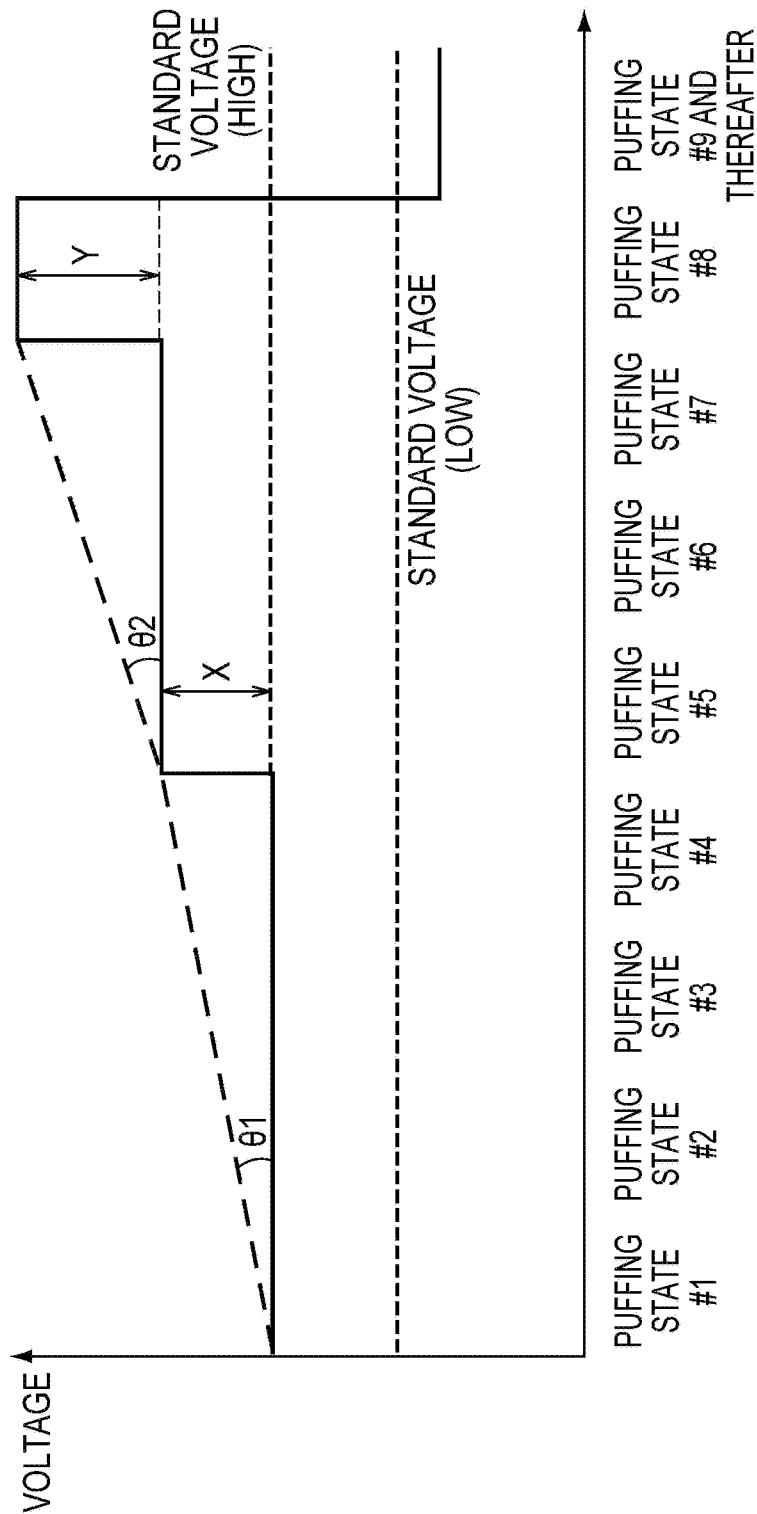
FIG. 9 is a diagram showing an example of power control in the puff action series according to the first embodiment.

An example of power control in a puff action series according to the first embodiment will be described, below. FIG. 8 and FIG. 9 are diagrams showing an example of power control in the puff action series according to the first embodiment. FIG. 8 and FIG. 9 illustrate a case in which the user must end a puff action series, in principle, when the number of times of the puff action reaches eight times (a predetermined number of times). Further, it must be noted that the behavior of the power source output in the non-puffing state is omitted in FIG. 8 and FIG. 9 since the power source output is not supplied to the heat source 80 in the non-puffing state.

Here, a case in which the power source output supplied to the heat source 80 is controlled depending on the voltage applied to the heat source 80 will be illustrated. Therefore, in the first embodiment, it may be assumed that the power source output is synonymous with voltage. Further, FIG. 8 shows the first mode (Low mode) in which a first voltage is used as the standard voltage, and FIG. 9 shows a second mode (High mode) in which a second voltage that is higher than the first voltage is used as the standard voltage. It is noted that the standard voltage is different, but the behavior of the voltage applied to the heat source 80 is similar in the first mode (Low mode) and the second mode (High mode).

As shown in FIG. 8 and FIG. 9, the heat source controller 53 gradually increases the voltage applied to the heat source 80 from the standard voltage with an increase in the number of times of the puff action of inhaling the aerosol. Specifically, in the puffing state #1 to the puffing state #4, the voltage applied to the heat source 80 is fixed, and the standard voltage is applied to the heat source 80. In the puffing state #5 to the puffing state #7, the voltage applied to the heat source 80 is fixed, and a voltage that is one step larger than the standard voltage is applied to the heat source 80. In the puffing state #8, a voltage that is two steps larger than the standard voltage is applied to the heat source 80. In the ninth puffing state and thereafter, a voltage that is smaller than the standard voltage is applied to the heat source 80.

As described above, the heat source controller 53 increases the gradient of the voltage applied to the heat source 80 with an increase in the number of times of the puff action of inhaling the aerosol.

For example, there is a reduction, with an increase in the number of times of the puff action, in the number of times of the puff action during which a fixed voltage is maintained. That is, the number of times of the puff action during which the standard voltage is applied is four, the number of times of the puff action during which a voltage that is one step larger than the standard voltage is applied is three, and the number of times of the puff action during which a voltage that is two steps larger than the standard voltage is applied is one. Alternatively, there is a reduction, with an increase in the number of times of the puff action, in the number of times of the puff action during which a fixed voltage is maintained. Alternatively, an increment Y of the voltage at the second time is larger than an increment X of the voltage of the first step.

As a result, there is an increase, with an increase in the number of times of the puff action, in the gradients ($\theta 1$ and $\theta 2$) of the voltage defined by the number of times of the puff action during which a fixed voltage is maintained, and the increment by which the voltage increases. In other words, the gradient $\theta 2$ of the middle stage of the puff action series is larger than the gradient $\theta 1$ of the initial stage of the puff action series.

In FIG. 8 and FIG. 9, the number of steps in which the voltage applied to the heat source 80 increases is two; however, the embodiment is not limited thereto. The number of steps in which the voltage applied to the heat source 80 increases may be three or more. Alternatively, the number of steps in which the voltage applied to the heat source 80 increases may be one.

(Power Control in One-Time Puff Action)

Figure 10:
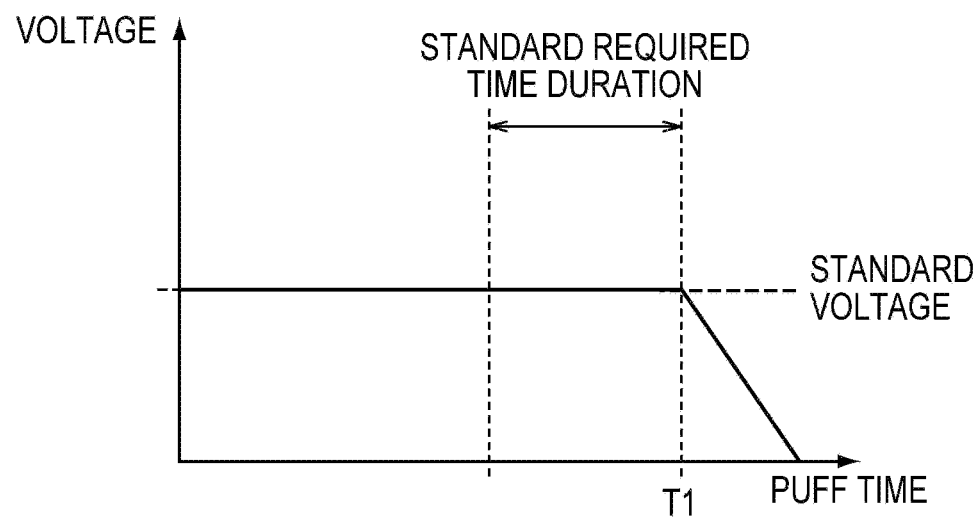
FIG. 10 is a diagram showing an example of power control in a one-time puff action according to the first embodiment.
Figure 11:
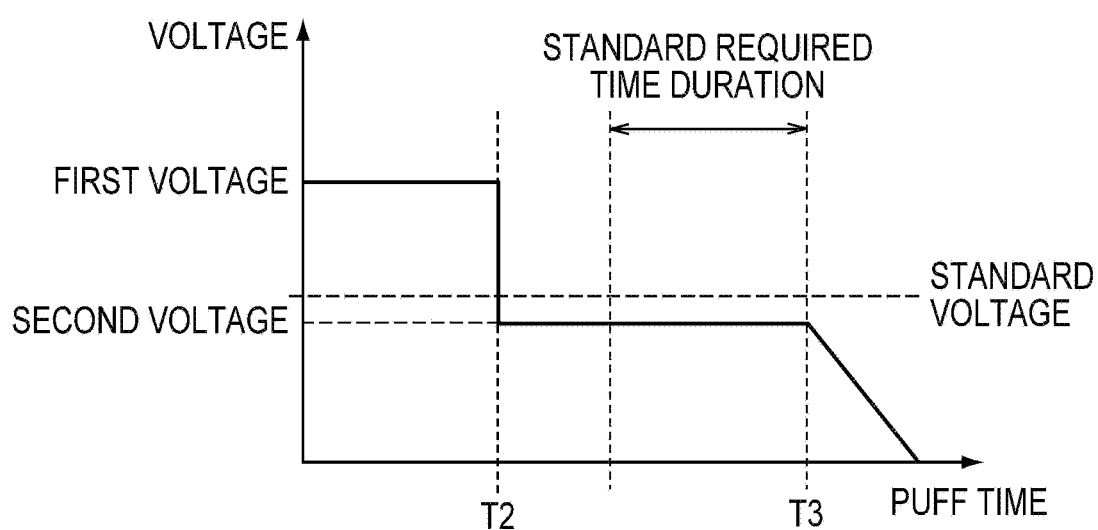
FIG. 11 is a diagram showing an example of power control in the one-time puff action according to the first embodiment.

An example of power control in a one-time puff action according to the first embodiment will be described, below. FIG. 10 and FIG. 11 are diagrams showing an example of power control in a one-time puff action according to the first embodiment. FIG. 10 and FIG. 11 illustrate a case in which the user must end a puff action series, in principle, when the number of times of the puff action reaches eight times (predetermined number of times).

Here, a case in which the power source output supplied to the heat source 80 is controlled depending on the voltage applied to the heat source 80 will be illustrated. Therefore, in the first embodiment, it may be assumed that the power source output is synonymous with voltage. Further, FIG. 10 shows a behavior of the voltage that is applied to the heat source 80 in the standard mode, and FIG. 11 shows a behavior of the voltage that is applied to the heat source 80 in the shortened mode.

As shown in FIG. 10, in the standard mode, the standard voltage is applied to the heat source 80 for the duration until a first time period T1 elapses. A voltage smaller than the standard voltage is applied to the heat source 80 for the duration after the first time period T1 has elapsed.

Here, a case is illustrated in which the first time period T1 is the same as the end timing of the standard required time duration. However, as described above, the first time period T1 is not limited thereto.

As shown in FIG. 11, in the shortened mode, a first voltage that is larger than the standard voltage is applied to the heat source 80 for the duration until a second time period T2 elapses. A second voltage that is smaller than the first voltage is applied to the heat source 80 for the duration until a third time period T3 after the second time period T2 elapses. A voltage smaller than the second voltage is applied to the heat source 80 for the duration after the third time period T3 has elapsed.

Here, a case is illustrated in which the second time period is shorter than the start timing of the standard required time duration. A case is illustrated in which the third time period is same as the end timing of the standard required time duration. A case is illustrated in which the second voltage is smaller than the standard voltage. However, as described above, the second time period T2, the third time period T3, and the second voltage are not limited thereto.

It is noted that a change in the required time of a one-time puff action is expected when the standard mode or the shortened mode has been set. Even in such a case, it must be noted that the voltage becomes zero at the same timing of the end of the puff action by tracing the profile of the voltage shown in FIG. 10 or FIG. 11. In other words, it must be noted that complex control such as continuous control of the amount of supply of the power source output on the basis of the air flow (inhalation rate) is unnecessary during the time when the power source output is being supplied to the heat source 80, since it may be favorable to control the power source output to the heat source according to the predetermined action mode.

(Operation and Effect)

In the first embodiment, the control circuit 50 (puff detection portion 51) detects the start or the end of the puff duration, when an inclination configured by two or more output values that are output from the sensor 20 has a predetermined sign (for example, negative), and an absolute value of the inclination having the predetermined sign is larger than a predetermined value. Therefore, it is possible to reduce the possibility of erroneously detecting, as the start of the puff duration, an output result of the sensor (for example, the pressure change at a high place, the vibration of human voice, etc.) that is originally not intended as the start of the puff duration, and the possibility of deterioration in the following capability of the power source output to the heat source 80, and thus, it is possible to enhance the detection accuracy of the puff duration. That is, it is possible to achieve both the improvement in the detection accuracy of the puff duration and the improvement in the following capability of the power source output.

In the first embodiment, when detecting the start or the end of the puff duration, the sensor 20 is used, configured to output electric capacitance of a capacitor that changes depending on the puff action of the user. As shown in FIG. 5, by focusing on a point that the pressure change within a housing configured to form an air flow path is specific in an early period and an ending period of inhaling action, then using a sensor capable of outputting such a pressure change, a response of detecting the puff duration is improved.

In the first embodiment, the sampling cycle ($\Delta$ta or $\Delta$tc) in which the output value that is output from the sensor 20 is monitored outside the puff duration is shorter than the sampling cycle ($\Delta$tb) in which the output value that is output from the sensor 20 is monitored within the puff duration. Thus, it is possible to reduce electric power necessary for monitoring the output value that is output from the sensor 20 in the puff duration while securing the following capability of the power source output with respect to the heat source 80 by maintaining the accuracy of detecting the start of the puff duration. It must be noted that there is no problem in that the accuracy of detecting the end of the puff duration is lower than the accuracy of detecting the start of the puff duration.

In the first embodiment, the control circuit 50 (puff detection portion 51) detects the start of the puff duration, when, for consecutive m times (m is an integer value of 2 or more) of S(n), a condition is satisfied before the detection of the start of the puff duration in which all S(n)s are a negative value, and the absolute value of all S(n)s is larger than the first value. On the other hand, the control circuit 50 (puff detection portion 51) detects the end of the puff duration, when, for consecutive m times of S(n), a condition is satisfied after the detection of the start of the puff duration in which S(n) is a negative value, and the absolute value of S(n) is larger than the first value. Thus, by using consecutive m times of S(n) when detecting the start or the end of the puff duration, it is possible to improve the detection accuracy of the puff duration.

In the first embodiment, in the non-puffing state in which aerosol is not inhaled, the light-emitting element controller 52 controls the light-emitting element 40 according to the second light-emitting mode that is different from the first light-emitting mode. As a result, even in the non-puffing state, it is possible to make the user understand whether or not the non-burning type flavor inhaler 100 is in a usable state. Further, since the light-emitting mode in the puffing state is different from the light-emitting mode in the non-puffing state, it is possible to realize a sense of use that resembles the sense of use of a regular cigarette in which aerosol is generated in association with burning.

In the first embodiment, the second light-emitting mode changes in accordance with the number of times of the puff action of inhaling aerosol. As a result, in the non-puffing state in which the emitted light of the light-emitting element 40 is easily visually recognized, the user is capable of easily understanding the progress status of puffing by the change in the second light-emitting mode.

In the first embodiment, the heat source controller 53 gradually increases the power source output to the heat source 80 from the standard power source output in association with an increase in the number of times of the puff action of inhaling the aerosol. As a result, it is possible to bring the amount of supply of the aerosol closer to the regular cigarette in which aerosol is generated in association with burning, and it is possible to realize a sense of use that resembles that of a regular cigarette.

In the first embodiment, the heat source controller 53 arranges the tobacco source 131 at the mouthpiece side from the holder 60 (aerosol source), and gradually increases the power source output to the heat source 80 from the standard power source output with an increase in the number of times of the puff action of inhaling the aerosol. As a result, it is possible to maintain an amount of supply of an alkaloid at a level close to an amount of supply of an alkaloid in an initial puff.

Specifically, with a configuration in which an alkaloid is contained in the aerosol source, such as an existing electric cigarette, the proportion of the alkaloid contained in the aerosol is constant. Therefore, in order to bring the amount of supply of the aerosol closer to that of the regular cigarette by using such a configuration, if the power source output to the heat source 80 is increased gradually from the standard power source output, then the amount of supply of the alkaloid increases in proportion with the amount of supply of the aerosol.

In contrast, in the first embodiment, a configuration is adopted in which the tobacco source 131 is arranged at the mouthpiece side from the holder 60 (aerosol source). The present inventors, etc. discovered a phenomenon by which the proportion of the alkaloid contained in the aerosol reduces with an increase in the number of times of puffing. As a result, in order to bring the amount of supply of the aerosol closer to that of the regular cigarette, if the power source output to the heat source 80 is increased gradually from the standard power source output, then the amount of supply of the alkaloid is maintained at a level close to the amount of supply of the alkaloid in the first puff.

Thus, in the first embodiment, in the configuration in which the tobacco source 131 is arranged at the mouthpiece side from the holder 60 (aerosol source), the heat source controller 53 gradually increases the power source output to the heat source 80 from the standard power source output with an increase in the number of times of the puff action of inhaling the aerosol. As a result, it is possible to maintain the amount of supply of the alkaloid at a level close to the amount of supply of the alkaloid in the first puff while bringing the amount of supply of the aerosol closer to that of the regular cigarette.

In the first embodiment, the heat source controller 53 controls a first mode in which a first standard power source output is used as the standard power source output, and a second mode in which a second standard power source output that is greater than the first standard power source output is used as the standard power source output. As a result, it is possible for the user to select an aerosol amount in accordance with a preference of the user, with a single non-burning type flavor inhaler 100.

In the first embodiment, even in the case of a user for whom the required time of a one-time puff action is shorter than the standard required time, it is possible to improve the level of satisfaction of such a user by raising the temperature of the heat source faster than the standard mode by introducing the shortened mode. Regardless of the action mode, since the power source output to the heat source is reduced for the duration after the first time period or the third time period has elapsed, inhaling of decomposed substances is prevented, and a drop in flavor is also prevented.

In the first embodiment, the predetermined action mode (standard mode and shortened mode) is provided, and thus it may be favorable to control the power source output to the heat source according to the predetermined action mode. As a result, during the period when power source output is being supplied to the heat source 80, complex control such as continuous control of the amount of supply of the power source output on the basis of the air flow (inhalation rate) is unnecessary. In other words, it is possible to realize a drop in the flavor, and an improvement in the level of satisfaction of the user, with a simple configuration.

First Modification

A first modification of the first embodiment will be described, below. Description proceeds with a particular focus on a difference from the first embodiment, below.

Specifically, in the above-described first embodiment, the heat source controller 53 controls the power source output to the heat source 80 from the power source 10 by controlling the voltage applied to the heat source 80 from the power source 10. In particular, the heat source controller 53 gradually increases the power source output (voltage) to the heat source 80 from the standard power source output (standard voltage) with an increase in the number of times of the puff action of inhaling the aerosol (see FIG. 9).

In contrast, in the first modification, the heat source controller 53 controls the voltage that is applied to the heat source 80 from the power source 10 by pulse control, and controls the power source output to the heat source 80 from the power source 10 by controlling the pulse width (Duty ratio) at which the voltage is applied to the heat source 80. In particular, the heat source controller 53 gradually shortens the pulse width at which the voltage is applied to the heat source 80 from the standard pulse width with an increase in the number of times of the puff action of inhaling the aerosol (see FIG. 12).

Figure 12:
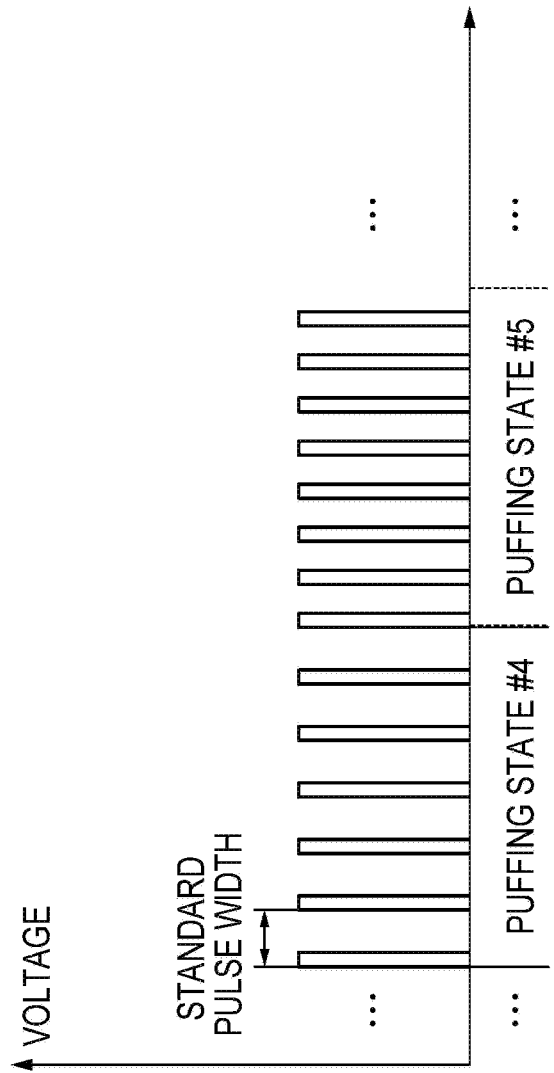
FIG. 12 is a diagram showing an example of power control in a puff action series according to a first modification of the first embodiment.

It is noted that following the example shown in FIG. 9, FIG. 12 illustrates a case in which the power source output is increased between the puffing state #4 and the puffing state #5. Although the puffing states other than the puffing state #4 and the puffing state #5 are omitted in FIG. 15, it is a matter of course that a similar effect as in the example shown in FIG. 9 is obtained by controlling the pulse width (Duty ratio).

Second Modification

A second modification of the first embodiment will be described, below. Description proceeds with a particular focus on a difference from the first embodiment, below.

Specifically, in the above-described first embodiment, the heat source controller 53 controls the power source output to the heat source 80 from the power source 10 by controlling the voltage applied to the heat source 80 from the power source 10. In particular, the heat source controller 53 gradually increases the power source output (voltage) to the heat source 80 from the standard power source output (standard voltage) with an increase in the number of times of the puff action of inhaling the aerosol (see FIG. 9).

Figure 13:
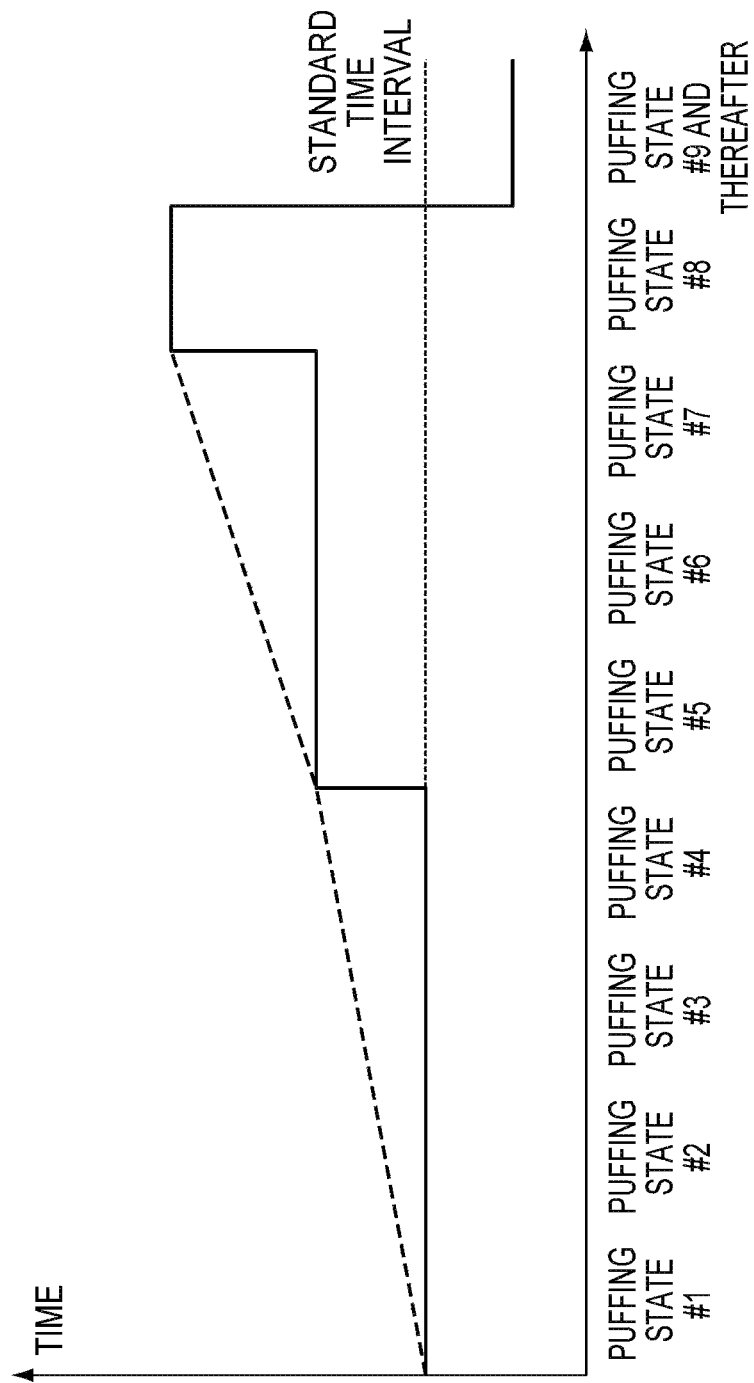
FIG. 13 is a diagram showing an example of power control in a puff action series according to a second modification of the first embodiment.

In contrast, in the second modification, the heat source controller 53 controls the power source output to the heat source 80 from the power source 10 by controlling the time interval during which the voltage is applied to the heat source 80. In particular, the heat source controller 53 gradually extends the time interval during which the voltage is applied to the heat source 80 from the standard time interval with an increase in the number of times of the puff action of inhaling the aerosol (see FIG. 13).

In the second modification, the standard time interval implies the maximum time for which the application of voltage to the heat source 80 is continued when the user continues the puff action. Therefore, if the time period during which the user continues the puff action exceeds the standard time interval, the application of voltage to the heat source 80 stops. It is noted that even if the application of voltage stops, the first light-emitting mode of the light-emitting element 40 is maintained during the time the puff action of the user continues. As a result, since the total power source output supplied to the heat source 80 in a one-time puff action changes, the similar effect as in the example shown in FIG. 9 is obtained.

It is noted that when the standard mode and the shortened mode described in the first embodiment are introduced, the first time period, the second time period, and the third time period may be adjusted (extended) with an increase in the number of times of the puff action of inhaling the aerosol.

Third Modification

A third modification of the first embodiment will be described, below. Description proceeds with a particular focus on a difference from the first embodiment, below.

Specifically, in the above-described first embodiment, as described in detail in the above-described first embodiment, the control circuit 50 (puff detection portion 51) detects the start of the puff duration, when, for consecutive m times (m is an integer value of 2 or more) of S(n), a condition is satisfied before the detection of the start of the puff duration in which all S(n)s are a negative value, and the absolute value of all S(n)s is larger than the first value. Thus, even in a case in which the user performs blowing from the mouthpiece of the non-burning type flavor inhaler 100 toward the inside of the non-burning type flavor inhaler 100, it is possible to reduce the possibility of erroneously detecting such an action as the start of the puff duration.

In contrast, a third modification further includes a means by which the blowing is detected when the user performs blowing, and the user is notified about the detection of blowing.

Specifically, the control circuit 50 (puff detection portion 51) detects the start of blowing, when, for consecutive m times of S(n), a condition is satisfied before the detection of the start of the puff duration in which all S(n)s are a positive value, and the absolute value of all S(n)s is larger than the first value. That is, in the third modification, the detection of blowing is performed by using the fact that the positive and negative signs are reversed in a sensor output pattern that is obtained when blowing is performed as compared to a pattern that is obtained when the puff action is performed.

When blowing is detected in the puff detection portion 51, the light-emitting controller 52 controls the light-emitting element 40 by a light-emitting mode that is different from the above-described first light-emitting mode and second light-emitting mode. That is, in the third modification, by controlling the light-emitting element 40 by a light-emitting mode that is different from the above-described first light-emitting mode and second light-emitting mode, the user is notified about the detection of blowing.

It is noted that, similarly to the case in the first embodiment, it is but natural that when blowing is detected in the puff detection portion 51, the heat source controller 53 does not perform the supply of power source output to the heat source 80 from the power source 10.

Second Embodiment

A second embodiment will be described, below. Description proceeds with a particular focus on a difference from the first embodiment, below.

Figure 14:
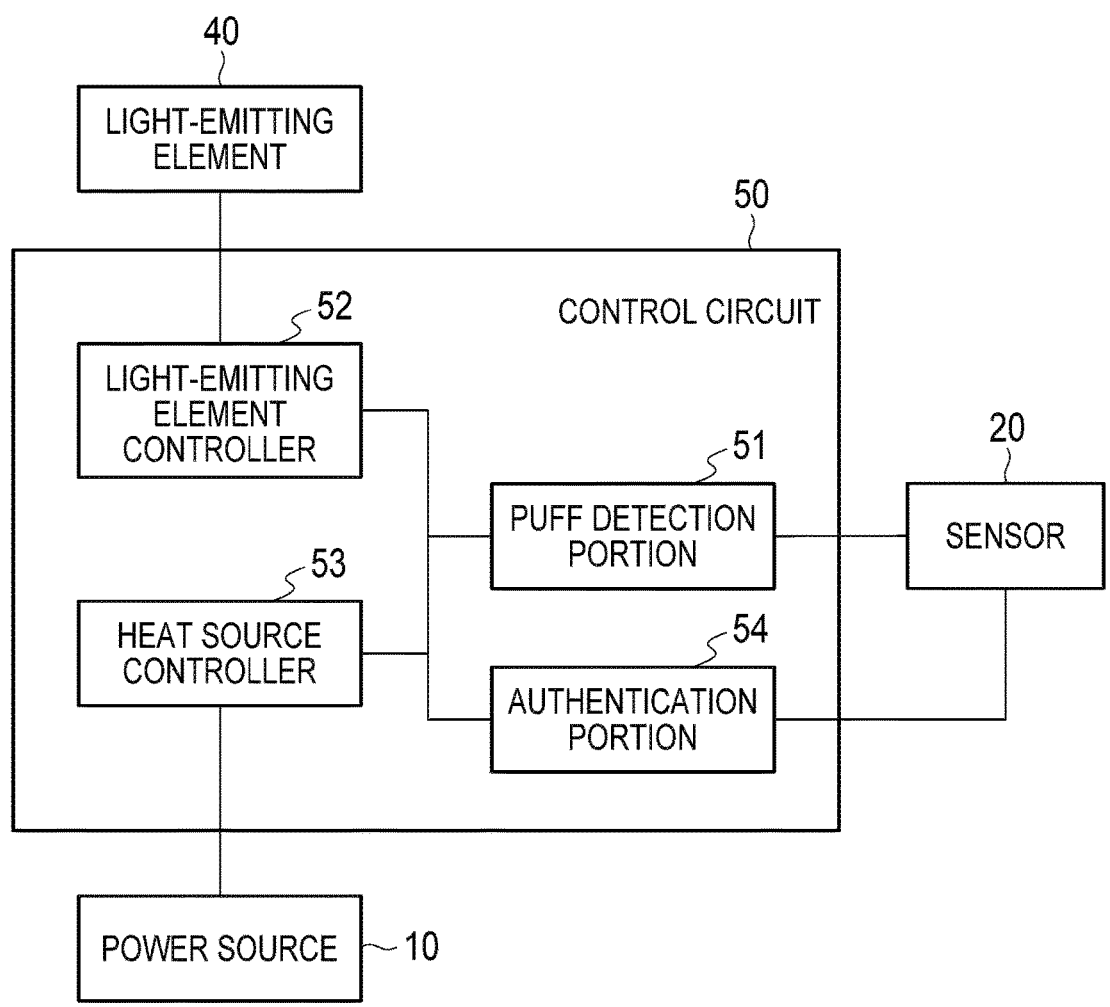
FIG. 14 is a block diagram showing a control circuit 50 according to a second embodiment.

In the first embodiment, the control circuit 50 (puff detection portion 51) detects the start of the puff duration by the inclination configured by two or more output values that are output from the sensor 20. In contrast, in the second embodiment, the control circuit 50 has an identification portion 54, as shown in FIG. 14.

Here, in the first embodiment, the output value that is output from the sensor 20 is a value showing the electric capacitance of a capacitor (for example, a voltage value or a current value). The response value that is derived from the output value is an output value itself that is output from the sensor 20. That is, the response value is a value indicating the electric capacitance of a capacitor (for example, a voltage value).

In contrast, in the second embodiment, the output value that is output from the sensor 20 is not restricted to a value indicating the electric capacitance of the capacitor, and may be a value that changes in accordance with the air inhaled from the mouthpiece side toward the non-mouthpiece side (that is, the puff action of the user). In other words, the output value that is output from the sensor 20 may be a value (for example, a voltage value or a current value) indicating an environment (for example, the pressure within a housing and the flow rate) that changes in accordance with the puff action of the user. The output value that is output from the sensor 20 may be a value itself indicating an environment that changes in accordance with the puff action of the user, or may be a value obtained by a predetermined conversion of the value. For example, the output value may be a flow rate value that is obtained through the conversion of the value (the value indicating the pressure) detected by the sensor 20. Likewise, the response value that is derived from the output value may be the output value itself that is output from the sensor 20, or may be a value obtained through a predetermined conversion of the output value that is output from the sensor 20 (for example, a flow rate value).

For example, when the output value is a flow rate value that is obtained through the conversion of a value indicating the pressure, the sensor 20 acquires the flow rate value on the basis of the amplitude or the frequency of a waveform that is obtained by plotting, on a time axis, the value (the value indicating the pressure) detected by the sensor 20. As a result, the sensor 20 is capable of outputting the flow rate value through a predetermined conversion of the value detected by the sensor 20. Further, in a case in which a capacitor microphone sensor described in the first embodiment is used as the sensor 20, when the response value is a flow rate value that is obtained through the conversion of a value indicating the pressure, the control circuit 50 acquires the flow rate value on the basis of the amplitude or the frequency of a waveform that is obtained by plotting, on a time axis, the output value (the value indicating the pressure) that is output from the sensor 20. As a result, it is possible to acquire a response value (for example, a flow rate value) through a predetermined conversion of the output value that is output from the sensor 20.

In particular, the control circuit 50 (puff detection portion 51) detects a puff action of the user when the response value derived from the output value that is output from the sensor 20 satisfies an inhaling condition. Further, the control circuit 50 (identification portion 54) identifies that the user is an authorized user when the response value derived from the output value that is output from the sensor 20 satisfies an identification condition.

Here, it must be noted that the identification condition differs from the response condition. "The identification condition differs from the response condition" may imply that the determination criteria (for example, a threshold value, or a value comparable with the threshold value) of whether or not the identification condition is satisfied is different from the determination criteria (for example, a threshold value, or a value comparable with the threshold value) of whether or not the inhaling condition is satisfied, or may imply that the determination timing of whether or not the identification condition is satisfied is different from the determination timing of whether or not the inhaling condition is satisfied. It is noted that when the determination timing of whether or not the identification condition is satisfied is different from the determination timing of whether or not the inhaling condition is satisfied, it is natural that the determination criteria of whether or not the identification condition is satisfied may be the same as the determination criteria of whether or not the inhaling condition is satisfied.

As described above, in the second embodiment, the control circuit 50 detects a puff action of the user when the response value derived from the output value that is output from the sensor 20 satisfies an inhaling condition, and the control circuit 50 identifies that the user is an authorized user when the response value derived from the output value that is output from the sensor 20 satisfies an identification condition.

In the second embodiment, the control circuit 50 determines, for each one-time puff action, whether or not the inhaling condition is satisfied and whether or not the identification condition is satisfied. The control circuit 50 preferably determines whether or not the identification condition is satisfied after the inhaling condition is satisfied.

Here, when the control circuit 50 determines whether or not the identification condition is satisfied after the inhaling condition is satisfied, the interval between the timing when the inhaling condition is satisfied and the timing at which it is determined whether or not the identification condition is satisfied (hereinafter, the determination interval) is preferably specified beforehand. The determination interval is, for example, 10 msec or more and 300 msec or less. The lower limit of the determination time is preferably 30 msec, and more preferably 50 msec. The upper limit of the determination time is preferably 200 msec, and more preferably 150 msec.

Firstly, the inhaling condition may be that the absolute value of a response value derived from an output value that is output from the sensor 20 exceeds a predetermined absolute value, and the identification condition may be that an inclination configured by two or more response values derived from an output value that is output from the sensor 20 exceeds a predetermined inclination. Here, a case in which the response value is a flow rate value is illustrated, but the response value may be a value indicating the pressure that is output from the sensor 20.

Figure 15:
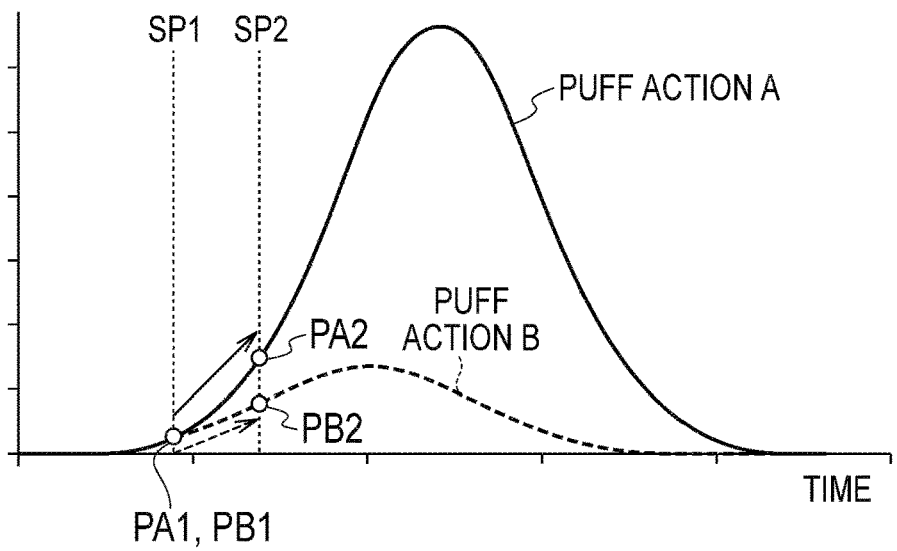
FIG. 15 is a diagram for describing user identification according to the second embodiment.

For example, as shown in FIG. 15, the description is provided by citing a puff action A and a puff action B having a different change mode of the response value (here, a flow rate value) as examples. For example, as for the puff action A, since an absolute value PA1 of the response value exceeds a predetermined absolute value in timing SP1, the inhaling condition is satisfied. Next, since an inclination configured by two or more response values (that is, an inclination of a straight line connecting the absolute value PA1 of a response value and an absolute value PA2 of a response value) exceeds a predetermined inclination in timing SP2, the identification condition is satisfied. On the other hand, as for the puff action B, since an absolute value PB1 of a response value exceeds the predetermined absolute value in timing SP1, the inhaling condition is satisfied. However, since an inclination configured by two or more response values (that is, an inclination of a straight line connecting the absolute value PB1 of a response value and an absolute value PB2 of a response value) does not exceed the predetermined inclination in timing SP2, the identification condition is not satisfied. It is noted that the interval (determination interval) between the timing (SP1) when the inhaling condition is satisfied and the timing (SP2) at which it is determined whether or not the identification condition is satisfied is, for example, specified beforehand.

In such a case, the control circuit 50 may start the supply of the power source output to the heat source 80 (atomizer) when the inhaling condition is satisfied. Alternatively, the control circuit 50 may start the supply of the power source output to the heat source 80 (atomizer) when the identification condition is satisfied.

In addition, the control circuit 50 may start the supply of power source output to the heat source 80 (atomizer) when the inhaling condition is satisfied, and the control circuit 50 may stop the supply of power source output to the heat source 80 (atomizer) when the identification condition is not satisfied after the inhaling condition is satisfied. It is noted that the control circuit 50 starts the supply of power source output to the heat source 80 (atomizer) when the inhaling condition is satisfied, and the control circuit 50 continues the supply of power source output to the heat source 80 (atomizer) when the identification condition is satisfied after the inhaling condition is satisfied.

Secondly, the inhaling condition may be that the absolute value of a response value derived from an output value that is output from the sensor 20 exceeds a first absolute value, and the identification condition may be that the absolute value of a response value derived from an output value that is output from the sensor 20 exceeds a second absolute value that is larger than the first absolute value. Here, a case in which the response value is a flow rate value is illustrated, but the response value may be a value indicating the pressure that is output from the sensor 20.

Figure 16:
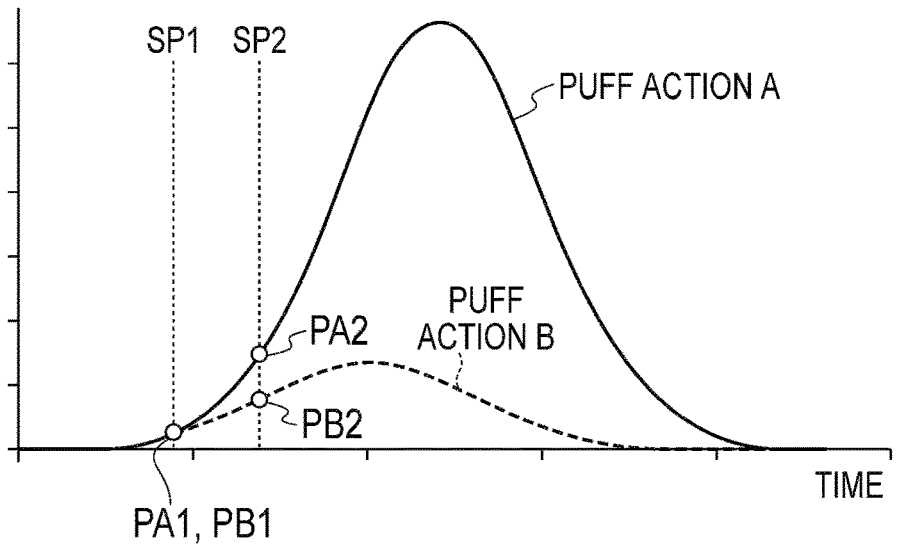
FIG. 16 is a diagram for describing the user identification according to the second embodiment.

For example, as shown in FIG. 16, the description is provided by citing the puff action A and the puff action B having a different change mode of the response value (here, a flow rate value) as examples. For example, as for the puff action A, since the absolute value PA1 of the response value exceeds the first absolute value in timing SP1, the inhaling condition is satisfied. Next, since the absolute value PA2 of the response value exceeds the second absolute value in timing SP2, the identification condition is satisfied. On the other hand, as for the puff action B, since the absolute value PB1 of the response value exceeds the first absolute value in timing SP1, the inhaling condition is satisfied. However, since the absolute value PB2 of the response value does not exceed the second absolute value in timing SP2, the identification condition is not satisfied. It is noted that the interval (determination interval) between the timing (SP1) when the inhaling condition is satisfied and the timing (SP2) at which it is determined whether or not the identification condition is satisfied is, for example, specified beforehand.

In such a case, the control circuit 50 may start the supply of the power source output to the heat source 80 (atomizer) when the inhaling condition is satisfied. Alternatively, the control circuit 50 may start the supply of the power source output to the heat source 80 (atomizer) when the identification condition is satisfied.

In addition, the control circuit 50 may start the supply of power source output to the heat source 80 (atomizer) when the inhaling condition is satisfied, and the control circuit 50 may stop the supply of power source output to the heat source 80 (atomizer) when the identification condition is not satisfied after the inhaling condition is satisfied. It is noted that the control circuit 50 starts the supply of power source output to the heat source 80 (atomizer) when the inhaling condition is satisfied, and the control circuit 50 continues the supply of power source output to the heat source 80 (atomizer) when the identification condition is satisfied after the inhaling condition is satisfied.

In the second embodiment, the non-burning type flavor inhaler 100 preferably notifies the user whether or not at least the inhaling condition is satisfied. For example, when the inhaling condition is satisfied, the control circuit 50 is capable of making the light-emitting element 40 emit light in a first mode (for example, the first light-emitting mode described in the first embodiment). Further, when the identification condition is also satisfied, the control circuit 50 may make the light-emitting element 40 emit light in a second mode (for example, the first light-emitting mode described in the first embodiment). The first mode may be same as the second mode, or may be different from the second mode. The control circuit 50 makes the light-emitting element 40 emit light in the first mode (for example, the first light-emitting mode described in the first embodiment) when the inhaling condition is satisfied, and makes the light-emitting element 40 emit light in a third mode (for example, a mode by which an identification error is notified) when the identification condition is not satisfied. Here, the third mode is, for example, blinking of the green-colored light-emitting element 40, and is different from the first mode and the second mode. The control circuit 50 makes the light-emitting element 40 emit light in a fourth mode (for example, the second light-emitting mode described in the first embodiment) when the inhaling condition is not satisfied. As a result, the user is capable of easily understanding whether or not the inhaling condition is satisfied, and whether or not the identification condition is satisfied.

(Operation and Effect)

In the second embodiment, the control circuit 50 detects a puff action of the user when the response value derived from the output value that is output from the sensor 20 satisfies the inhaling condition, and the control circuit 50 identifies that the user is an authorized user when the response value derived from the output value that is output from the sensor 20 satisfies the identification condition. That is, since user identification is performed by using the sensor 20 for detecting the puff action, it is possible to implement user identification while preventing an increase in the number of components for performing user identification.

In the second embodiment, the control circuit 50 determines, for each one-time puff action, whether or not the inhaling condition is satisfied and whether or not the identification condition is satisfied. Since user identification is performed for each puff action, it is possible to effectively prevent unauthorized use by an unauthorized user.

In the second embodiment, the control circuit 50 starts the supply of the power source output to the heat source 80 (atomizer) when the identification condition is satisfied. Therefore, it is possible to prevent an inhaling of aerosol by an unauthorized user.

In the second embodiment, the control circuit 50 starts the supply of power source output to the heat source 80 (atomizer) when the inhaling condition is satisfied, and the control circuit 50 stops the supply of power source output to the heat source 80 (atomizer) when the identification condition is not satisfied after the inhaling condition is satisfied. Therefore, since the supply of power source output to the heat source 80 (atomizer) starts without waiting for the timing when the identification condition is satisfied, it is possible to quickly raise the temperature of the heat source 80 (atomizer) in accordance with the detection of the puff action of the user, and it is possible to effectively prevent unauthorized use by an unauthorized user.

In the second embodiment, the control circuit 50 starts the supply of power source output to the heat source 80 (atomizer) when the inhaling condition is satisfied, and the control circuit 50 continues the supply of power source output to the heat source 80 (atomizer) when the identification condition is satisfied after the inhaling condition is satisfied. Therefore, since the supply of power source output to the heat source 80 (atomizer) starts without waiting for the timing when the identification condition is satisfied, it is possible to quickly raise the temperature of the heat source 80 (atomizer) in accordance with the detection of the puff action of the user, and it is possible to prevent the delay in the delivery of the aerosol to an authorized user.

First Modification

A first modification of the second embodiment will be described, below. Description proceeds with a particular focus on a difference from second first embodiment, below.

Specifically, in the first modification, the control circuit 50 (identification portion 54) uses a first identification condition as an identification condition in a first puff action, and uses a second identification condition that is different from the first identification condition as an identification condition in a second puff action preformed after the first identification condition is satisfied. The second identification condition is preferably a condition that is satisfied more easily than the first identification condition. In particular, the second identification condition may be a condition that is satisfied easily at a stage earlier than the first identification condition, in a one-time puff action. Alternatively, the second identification condition may be a condition that is satisfied easily in a continuous manner as compared to the first identification condition, in different puff actions.

The first identification condition may be, for example, the same as the identification condition described in the second embodiment. That is, the first identification condition may be that an inclination configured by two or more response values derived from an output value that is output from the sensor 20 exceeds a predetermined inclination, or that the absolute value of a response value derived from an output value that is output from the sensor 20 exceeds the second absolute value.

The second identification condition may be, for example, the same as the inhaling condition described in the second embodiment. That is, the second identification condition may be that the absolute value of a response value derived from an output value that is output from the sensor 20 exceeds a predetermined absolute value, or that the absolute value of a response value derived from an output value that is output from the sensor 20 exceeds the first absolute value.

Here, when a specific condition is satisfied after the first identification condition is satisfied, the control circuit 50 (identification portion 54) may use the first identification condition rather than the second identification condition. The specific condition is a condition in which it is considered that a puff action series has ended. A puff action series is a series of actions in which the puff action is repeated a predetermined number of times. It must be noted that in a puff action series, the interval of each puff action is shorter than a predetermined interval. In other words, the specific condition is a condition in which it is considered that there is a possibility of a different user using the non-burning type flavor inhaler 100. Specifically, the specific condition may be that the power source of the non-burning type flavor inhaler 100 is disconnected, or may be that a predetermined time period elapses while a puff action is not being performed from the time a puff action is performed.

(Operation and Effect)

In the first modification, the control circuit 50 uses the first identification condition as an identification condition in the first puff action, and uses the second identification condition that is different from the first identification condition as an identification condition in the second puff action performed after the first identification condition is satisfied. In other words, by maintaining a high accuracy of user identification in the first puff action while using the second identification condition that is easier to satisfy than the first identification in the second puff action, it becomes possible to prevent a delay in the delivery of the aerosol to an authorized user.

In the first modification, when a specific condition is satisfied after the first identification condition is satisfied, the control circuit 50 uses the first identification condition rather than the second identification condition. Therefore, by using the first identification condition that is more difficult to satisfy than the second identification condition, it is possible to prevent the unauthorized use by an unauthorized user.

Second Modification

A second modification of the second embodiment will be described, below. Description proceeds with a particular focus on a difference from second first embodiment, below.

In the second embodiment, the control circuit 50 determines, for each one-time puff action, whether or not the inhaling condition is satisfied and whether or not the identification condition is satisfied. In contrast, in the second modification, the control circuit 50 has an action mode by which the supply of power source output to the heat source 80 (atomizer) is performed on the basis of a response value derived from an output value that is output from the sensor 20, and an identification mode by which it is determined whether or not the identification condition is satisfied on the basis of a response value derived from an output value that is output from the sensor 20. The action mode starts after the identification condition is satisfied in the identification mode. It is noted that the action mode ends at a timing when it is considered that the puff action series has ended. In other words, the action mode ends at the timing when it is considered that there is a possibility of a different user using the non-burning type flavor inhaler 100. Specifically, the action mode may end in accordance with a disconnection of the power source of the non-burning type flavor inhaler 100, or may end when a predetermined time period elapses while a puff action is not being performed from the time a puff action is performed. It is preferable that the identification mode starts again once the action mode ends.

In particular, in the identification mode, the control circuit 50 (identification portion 54) determines whether or not the identification condition is satisfied, on the basis of whether or not a profile that is represented by two or more response values in a space (hereinafter, a predetermined coordinate space) defined by a first axis indicating a size of a response value and a second axis indicating a time length corresponds to an identification profile.

For example, the identification profile is defined by the absolute value of a response value, by whether or not the response value is a value based on inhaling, by whether or not the response value is a value based on blowing, by the sampling cycle of a response value, or by one or more parameters selected from among these parameters. By using the above-described parameters, it is possible to define the identification profile by, for example, the number of times of inhaling within a fixed time period, the number of times of blowing within a fixed time period, a combination of inhaling and blowing within a fixed period, a time length of a one-time inhaling, a time length of a one-time blowing, a maximum flow rate value of a one-time inhaling, a maximum flow rate value of a one-time blowing, an inclination configured by two or more flow rate values in a one-time inhaling, or an inclination configured by two or more flow rate values in a one-time blowing. For example, the lower limit of the above-described fixed time period is 0.1 second, and the upper limit of the fixed time period is 5 seconds. The lower limit of the fixed time period may be 0.3 second, or may be 0.5 second. The upper limit of the fixed time period may be 3 seconds.

Figure 17:
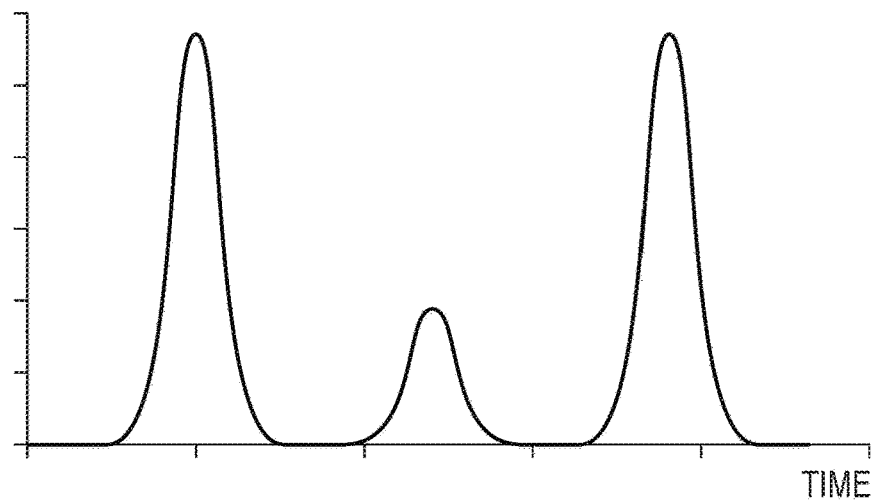
FIG. 17 is a diagram for describing user identification according to a second modification of the second embodiment.
Figure 18:
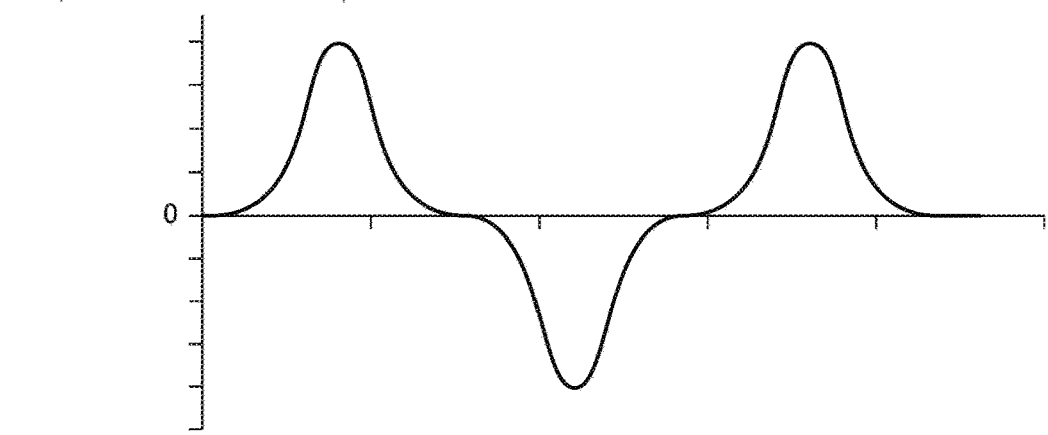
FIG. 18 is a diagram for describing the user identification according to a second modification of the second embodiment.

For example, as shown in FIG. 17, the identification profile may be defined by a combination of a plurality of times of inhaling having mutually different maximum flow rate values of a one-time blowing. Alternatively, as shown in FIG. 18, the identification profile may be defined by a combination of inhaling and blowing within a fixed time period. It must be noted that in FIG. 18, a profile projected upward represents a profile based on inhaling, and a profile projected downward represents a profile based on blowing.

The identification profile may be registered beforehand, or may be registered by the user. When the identification profile is registered by the user, the control circuit 50 preferably has a registration mode in addition to the action mode and the identification mode. The control circuit 50 registers a response value derived from the output value that is output from the sensor 20 in the registration mode as the identification profile.

The control circuit 50 transits to the registration mode by, for example, the above-described operation of the push button 30, or an operation using the sensor 20.

In the second modification, in the action mode, the control circuit 50 preferably starts the supply of power source output to the heat source 80 (atomizer) when the inhaling condition described in the second embodiment is satisfied. However, in the action mode, the control circuit 50 may start the supply of power source output to the heat source 80 (atomizer) when the identification condition described in the second embodiment is satisfied. It must be noted that the identification condition (identification profile) used in the identification mode differs from the identification condition used in the action mode. In such a cases, it must be noted that the control circuit 50 determines whether or not the inhaling condition (or the identification condition) is satisfied for each one-time puff action.

(Operation and Effect)

In the second modification, the control circuit 50 has an action mode by which the supply of power source output to the heat source 80 (atomizer) is performed on the basis of a response value derived from an output value output from the sensor 20, and an identification mode by which it is determined whether or not the identification condition is satisfied on the basis of a response value derived from an output value output from the sensor 20. Therefore, similarly to the second embodiment, it is possible to implement user identification while avoiding an increase in the number of components. In addition, by the introduction of the identification mode, it is possible to skip user identification for each puff action, and thus, it is possible to prevent a delay in the delivery to an authorized user.

In the second modification, in the identification mode, the control circuit 50 (identification portion 54) determines whether or not the identification condition is satisfied, on the basis of whether or not a profile that is represented by two or more response values in a predetermined coordinate space corresponds to the identification profile. The identification profile is used to determine whether or not the identification condition is satisfied, and thus, the accuracy of user identification improves.

Third Modification

A third modification of the second embodiment will be described, below. Description proceeds with a particular focus on a difference from second embodiment, below.

In the third modification, the control circuit 50 ends the action mode when the profile represented by two or more response values in the predetermined coordinate space corresponds to a cancellation profile. It must be noted that when the action mode ends, and when a response value corresponding to the identification profile is not outputted from the sensor 20 in the identification mode, the supply of power source output to the heat source 80 (atomizer) is not performed.

Here, the cancellation profile may be registered beforehand, or may be registered by the user. The cancellation profile may be the same as the identification profile.

In such a case, the control circuit 50 preferably has a cancellation mode in addition to the action mode and the identification mode. The control circuit 50 transits to the cancellation mode by, for example, the above-described operation of the push button 30, or an operation using the sensor 20. It must be noted that in the cancellation mode, the control circuit 50 receives a response value that must be compared to the cancellation profile.

Alternatively, the control circuit 50 resets the identification profile when the profile represented by two or more response values in the predetermined coordinate space corresponds to a reset profile. The reset of the identification profile is a process of returning the identification profile to an initial state (for example, the factory default state). For example, when the identification profile is registered beforehand in the initial state, the reset of the identification profile is a process of returning the identification profile that is currently registered to the identification profile that is registered beforehand in the initial state. Alternatively, when the identification profile is not registered beforehand in the initial state, the reset of the identification profile is a process of returning to the state in which the identification profile is not registered. Alternatively, regardless of whether or not the identification profile is registered beforehand in the initial state, the reset of the identification profile may be a process of deleting the identification profile used in the identification mode. Noted that it is natural that even after the identification profile is deleted, the identification profile may be registered again.

Here, the reset profile may be registered beforehand, or may be registered by the user. The reset profile may be the same as the identification profile. The reset profile is preferably an identification profile that is registered beforehand in the initial state (for example, the factory default state).

In such a case, the control circuit 50 preferably has a reset mode in addition to the action mode and the identification mode. The control circuit 50 transits to the reset mode by, for example, the above-described operation of the push button 30, or an operation using the sensor 20. It must be noted that in the reset mode, the control circuit 50 receives a response value that must be compared to the reset profile.

In the third modification, the non-burning type flavor inhaler 100 may have a notification portion configured to notify the user of the cancellation profile or the reset profile. The notification portion is, for example, the light-emitting element 40, and the light-emitting element 40 notifies the user of the cancellation profile or the reset profile by a light-emitting pattern of the light-emitting element 40. It is noted that the notification of the cancellation profile or the reset profile is preferably performed in accordance with a predetermined operation that is different from inhaling (or blowing) corresponding to the identification profile. For example, if the non-burning type flavor inhaler 100 is connectable to an external device (a personal computer and a smartphone), the notification of the cancellation profile or the reset profile is preferably performed when a correct password is entered in the external device. Alternatively, the notification of the cancellation profile or the reset profile is preferably performed when an operation in which the push button 30 is pushed according to a predetermined pattern is performed. The predetermined pattern is preferably specified in the instruction manual of the non-burning type flavor inhaler 100.

In the third modification, a case is illustrated in which the cancellation mode and the reset mode are prepared; however, these modes may not necessarily be prepared. That is, the control circuit 50 may receive the cancellation profile and the reset profile during the action mode.

It is noted that, similarly to the identification profile, the cancellation profile and the reset profile are defined, for example, by the absolute value of a response value, by whether or not the response value is a value based on inhaling, by whether or not the response value is a value based on blowing, by the sampling cycle of a response value, or by one or more parameters selected from among these parameters. By using these parameters, it is possible to define the cancellation profile and the reset profile by, for example, the number of times of inhaling within a fixed time period, the number of times of blowing within a fixed time period, a combination of inhaling and blowing within a fixed period, a time length of a one-time inhaling, a time length of a one-time blowing, a maximum flow rate value of a one-time inhaling, a maximum flow rate value of a one-time blowing, an inclination configured by two or more flow rate values in a one-time inhaling, or an inclination configured by two or more flow rate values in a one-time blowing.

(Operation and Effect)

In the third modification, the control circuit 50 ends the action mode when the profile represented by two or more response values in the predetermined coordinate space corresponds to the cancellation profile. Therefore, it is possible to prevent the non-burning type flavor inhaler 100 from being left in a state in which the user is identified as an authorized user, that is, in a state in which the action mode is continuing. As a result, it is possible to prevent an unauthorized use by an unauthorized user.

In the third modification, the control circuit 50 resets the identification profile when the profile represented by two or more response values in the predetermined coordinate space corresponds to the reset profile. Therefore, the authorized user is capable of returning the identification profile to the initial state. As a result, even when the authorized user forgets the identification profile, if the reset profile is a known profile that is different from the identification profile, then it is possible to continue to use the non-burning type flavor inhaler 100. In addition, even in a case when the authorized user forgets the identification profile registered arbitrarily by the authorized user, if the reset profile is an identification profile that is registered beforehand in the initial state (for example, the factory default state), then it is possible to continue to use the non-burning type flavor inhaler 100.

In the third modification, the non-burning type flavor inhaler 100 has the notification portion configured to notify the user of the cancellation profile or the reset profile. As a result, even when the authorized user forgets the identification profile, it is possible to continue to use the non-burning type flavor inhaler 100.

Fourth Modification

A fourth modification of the second embodiment will be described, below. Description proceeds with a particular focus on a difference from second first embodiment, below.

Figure 19:
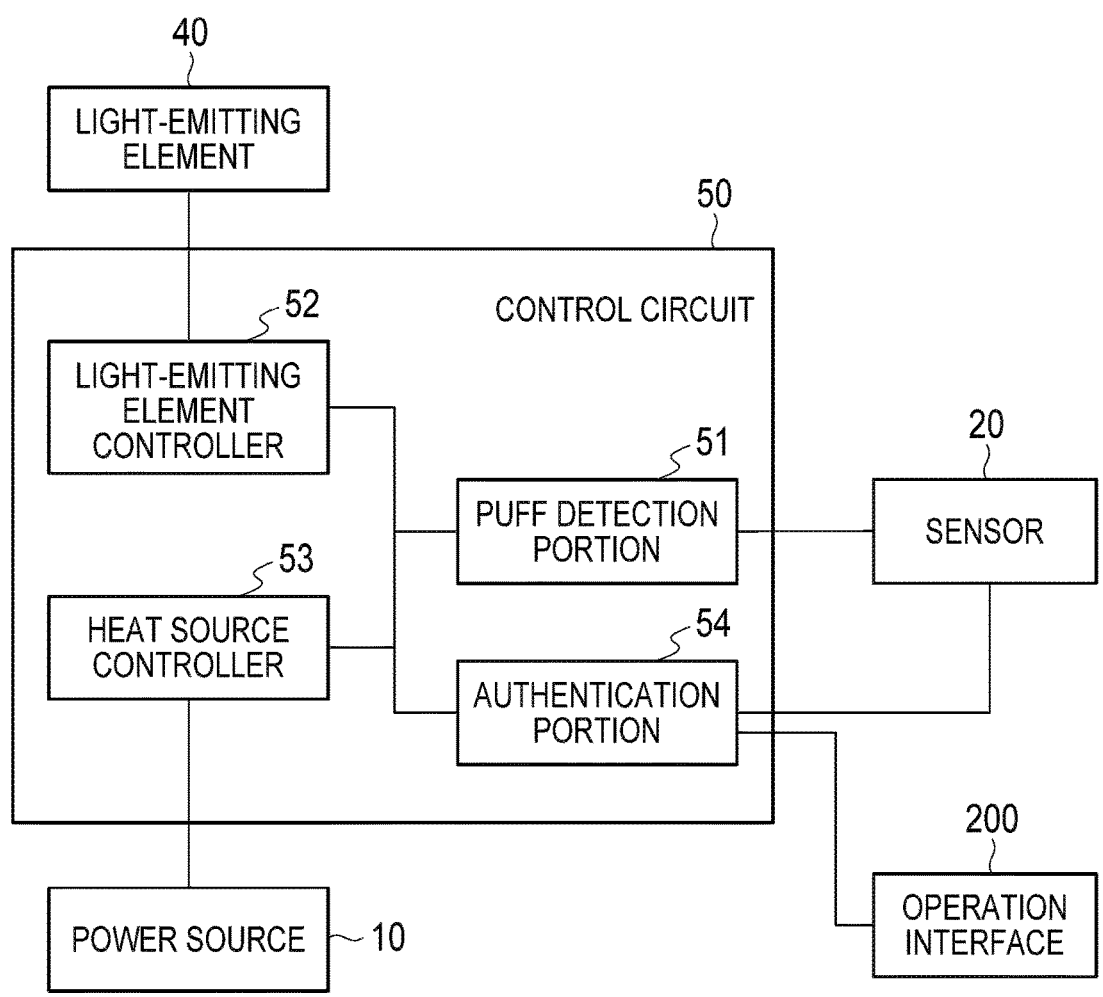
FIG. 19 is a block diagram showing a control circuit 50 according to a fourth modification of the second embodiment.

In the fourth modification, the control circuit 50 determines, on the basis of a stringency selected from among a plurality of stages of stringency, whether or not the profile represented by two or more response values in the predetermined coordinate space corresponds to the identification profile. Further, as shown in FIG. 19, the non-burning type flavor inhaler 100 has an operation interface 200. The operation interface 200 is an interface for switching the plurality of stages of stringency. It is noted that the operation interface 200 may be configured by a button, may be configured by a sliding-type lever, or may be configured by a circular dial. However, the operation interface 200 preferably has a protect function for enabling the operation of the operation interface 200. The protect strength of the protect function is an arbitrary value.

Here, the "stringency" is, for example, a standard that must be satisfied by the level of coincidence of the profile represented by two or more response values in the predetermined coordinate space, and the identification profile. For example, the level of coincidence of the profile represented by two or more response values in the predetermined coordinate space, and the identification profile is possible to be expressed in the numerical form by pattern matching, and the stringency is a threshold value comparable to the level of coincidence expressed in the numerical form.

It is noted that the control circuit 50 may determines, on the basis of the stringency selected from among the plurality of stages of stringency, whether or not the profile represented by two or more response values in the predetermined coordinate space corresponds to the cancellation profile or the reset profile. Even in such a case, the plurality of stages of stringency are switched by the operation interface 200.

Here, the plurality of stages of stringency may be switched automatically such that the stringency is alleviated over time in response to the failure of user identification. However, if user identification fails in a state in which the stringency is the most alleviated, the non-burning type flavor inhaler 100 may be set to a locked state in which the non-burning type flavor inhaler 100 is not possible to be used (for example, a state in which the supply of power source output to the heat source 80 (atomizer) is not performed unless the locked state is canceled). The locked state, for example, is canceled when inhaling (or blowing) corresponding to the identification profile that is registered beforehand in the initial state (for example, the factory default state) is performed.

(Operation and Effect)

In the fourth modification, the control circuit 50 determines, on the basis of the stringency selected from among the plurality of stages of stringency, whether or not the profile represented by two or more response values in the predetermined coordinate space corresponds to the identification profile, and the plurality of stages of stringency are switched by the operation interface 200. Therefore, it is possible to strike a balance between an appropriate control of use by an authorized user, and a reduction in the complexity of user identification, in accordance with the use scenes of the non-burning type flavor inhaler 100.

Fifth Modification

A fifth modification of the second embodiment will be described, below. Description proceeds with a particular focus on a difference from second first embodiment, below.

Figure 20:
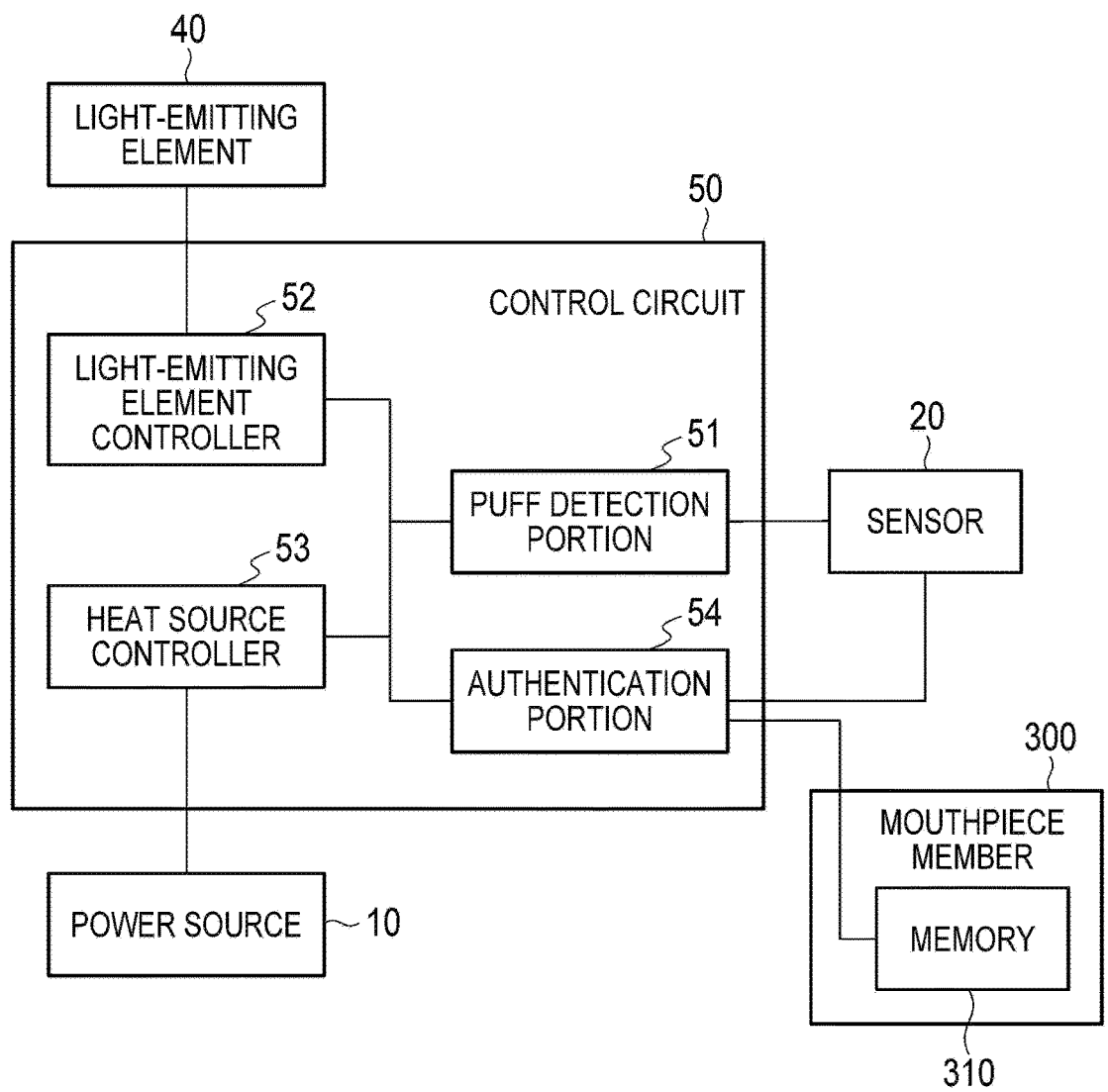
FIG. 20 is a block diagram showing a control circuit 50 according to a fifth modification of the second embodiment.

In the fifth modification, as shown in FIG. 20, the non-burning type flavor inhaler 100 has a mouthpiece member 300 that is configured in a replaceable manner with respect to the housing (the outer wall 124 of the atomization unit 120 described in the first embodiment) having the air flow path 122. The mouthpiece member 300 has a memory 310 including a memory configured to store the identification profile. The memory 310 may store the cancellation profile or the reset profile.

Here, the mouthpiece member 300 is, for example, the mouthpiece unit 140 described in the first embodiment. It must be noted that the mouthpiece member 300 is replaced when, for example, a different user uses the non-burning type flavor inhaler 100 (for example, the electrical unit 110 and the atomization unit 120, etc.). The mouthpiece unit 140 may not necessarily be replaced even when the capsule unit 130 described in the first embodiment is replaced.

It is noted that the mouthpiece member 300 having the memory 310 may be a unit including the mouthpiece. For example, when a cartridge having at least either one of the flavor source or the atomizer has a mouthpiece, the mouthpiece member 300 having the memory 310 may be such a cartridge. However, the fifth modification is not restricted thereto, and the memory 310 may be provided in a unit that does not have a mouthpiece. For example, even when a cartridge having at least either one of the flavor source or the atomizer does not have a mouthpiece, the memory 310 may be provided in such a cartridge.

(Operation and Effect)

In the fifth modification, the mouthpiece member 300 that is configured in a replaceable manner with respect to the housing has the memory 310 configured to store the identification profile. Therefore, it is possible to use a different identification profile for each user. Further, by removing the mouthpiece member 300, it is possible to prevent an unauthorized use by an unauthorized user.

Other Embodiments

The present invention is described through the above-described embodiments, but it should not be understood that this invention is limited by the statements and the drawings constituting a part of this disclosure. From this disclosure, various alternative embodiments, examples, and operational technologies will become apparent to those skilled in the art.

Although not particularly mentioned in the embodiments, the non-burning type flavor inhaler 100 may be connectable to an external device (a personal computer and a smartphone). In such a case, the registration of the identification profile may be performed by using the external device. Alternatively, the cancellation of the state in which the user is identified as an authorized user may be performed by using the external device. Else, the reset of the identification profile may be performed by using the external device.

In the embodiments, the transition to the registration mode, the cancellation mode, and the reset mode, etc. is performed by an operation of the push button 30. However, the embodiment is not limited thereto. If the non-burning type flavor inhaler 100 is connectable to an external device (a personal computer and a smartphone), the transition to the registration mode, the cancellation mode, and the reset mode, etc. may be performed by using an external device.

In the embodiments, the tobacco source 131 is illustrated as the flavor source. However, the embodiment is not limited thereto. The flavor source may not necessarily include a tobacco raw material. In addition, the non-burning type flavor inhaler 100 may not have a flavor source, and an inhaling flavor component may be added to the aerosol source.

In the embodiments, a case is illustrated in which the non-burning type flavor inhaler 100 has the capsule unit 130. However, the embodiment is not limited thereto. For example, the non-burning type flavor inhaler 100 may have a cartridge containing the flavor source.

In the embodiments, a case is illustrated in which the puff detection portion 51 detects the start or the end of the puff duration, when the inclination configured by two or more response values that are output from the sensor 20 has a negative sign, and the absolute value of the inclination having a negative sign is larger than a predetermined value. However, the embodiment is not limited thereto. Specifically, the puff detection portion 51 may detect the start or the end of the puff duration, when the inclination configured by two or more response values that are output from the sensor 20 has a positive sign, and the absolute value of the inclination having a positive sign is larger than a predetermined value. In such a case, the expression "negative" in the embodiments may be replaced by "positive". Consideration must be given to the fact that which one of "positive" and "negative" needs to be applied depends on the type of the sensor 20, etc., that is, depends on an output pattern of the sensor 20 with respect to the puff action of the user.

Although not particularly specified in the embodiments, the push button 30 configures a switch member for starting and stopping the supply of electric power to the control circuit 50 and the sensor 20 from the power source 10. Since the supply of power to the sensor 20 is stopped by pushing the push button 30, it is possible to realize a reduction in the consumption of electric power.

Although not particularly specified in the embodiments, when the power value that is monitored at the sampling cycle Δta does not change over a predetermined time period (for example, 200 msec. to 500 msec.) before the start of the puff duration is detected, the sensor 20 may be turned OFF. As a result, it is possible to realize energy-saving. Further, in such a case, it is preferable to turn ON the sensor 20 when a predetermined time period (for example, 50 msec.) has elapsed since turning OFF the sensor 20. As a result, it is possible to secure the following capability of the power supply with respect to the heat source 80 while saving energy. It must be noted that when the power value that is monitored at the sampling cycle Δta changes, the sensor 20 is turned ON continuously. It is noted that, as a behavior different from the ON/OFF behavior of such a sensor 20, the sensor 20 may be repeatedly turned ON/OFF in synchronization with the sampling cycle (Δt) and the calculation cycle of S(n).

In the embodiments, although not particularly mentioned, since the tobacco source 131 is held within the capsule unit 130, the pH of the tobacco raw material contained in the tobacco source 131 may be changed for each capsule unit 130. In such a case, depending on the type of the capsule unit 130, the gradient of the power source output to the heat source 80 may be changed with an increase in the number of times of the puff action.

In the embodiments, although not particularly mentioned, the number of times of the puff action may be corrected by a value (the amount of generation of the aerosol) defined by the power source output to the heat source 80 in a one-time puff action. Specifically, if the amount of aerosol generated in a one-time puff action is smaller than the default value, the number of times of the puff action may be accumulated by adding a value obtained by multiplying a predetermined coefficient α (α<1) once. On the other hand, if the amount of aerosol generated in a one-time puff action is greater than the default value, the number of times of the puff action may be accumulated by adding a value obtained by multiplying a predetermined coefficient β(β>1) once. That is, the number of times of the puff action need not necessarily be an integer.

In the embodiments, although not particularly mentioned, in the power control of the puff action series, the timing of increasing the power source output to the heat source 80 is preferably synchronized with the timing of changing the second light-emitting mode. For example, as shown in FIG. 8 and FIG. 9, when the power source output (voltage) to the heat source 80 is increased between the puffing state #4 and the puffing state #5, the second light-emitting mode preferably changes between the puffing state #4 and the puffing state #5.

In the embodiments, although not particularly specified, as shown in FIG. 10 and FIG. 11, a voltage that is smaller than the standard voltage is applied to the heat source 80 for the duration after the first time period T1 or the third time period T3 has elapsed; however, the first light-emitting mode preferably continues even for such a duration.

In the embodiments, the first mode (Low mode shown in FIG. 8) in which the first standard power source output is used as the standard power source output, and the second mode (High mode shown in FIG. 9) in which the second standard power source output that is greater than the first standard power source output is used as the standard power source output, are provided. In such a case, the light-emitting mode of the first mode may be different from the light-emitting mode of the second mode. That is, each of the first light-emitting mode, the second light-emitting mode, and the end light-emitting mode of the first mode may be different from the first light-emitting mode, the second light-emitting mode, and the end light-emitting mode of the second mode.

Although not particularly mentioned in the embodiments, a program may be provided, configured to cause a computer to execute each process performed by the non-burning type flavor inhaler 100. Further, the program may be recorded on a computer-readable medium. By using the computer-readable medium, it is possible to install the program in a computer. Here, the computer-readable medium in which the program is recorded thereon may include a non-transitory recording medium. The non-transitory recording medium is not particularly limited; the non-transitory recording medium may include a recording medium such as a CD-ROM or a DVD-ROM, for example.

Alternatively, a chip may be provided which is configured by: a memory in which a program for executing each process performed by the non-burning type flavor inhaler 100 is stored; and a processor configured to execute the program stored in the memory.

It is noted that the entire content of Japanese Patent Application No. 2014-095164 (filed on May 2, 2014) is incorporated in the subject application by reference.

INDUSTRIAL APPLICABILITY

According to the embodiments, it is possible to provide a non-burning type flavor inhaler by which it is possible to implement user identification while avoiding an increase in the number of components.

The invention claimed is:

1. A non-burning type flavor inhaler, comprising:
a housing having an air flow path that continues from an inlet to an outlet;
an atomizer configured to atomize an aerosol source without burning;
a sensor configured to output a value that changes in accordance with a puff action of a user; and
a controller configured to detect a puff action of the user when a response value derived from a value that is output from the sensor satisfies an inhaling condition, the controller configured to identify that the user is an authorized user when the response value satisfies an identification condition that is different from the inhaling condition.

2. The non-burning type flavor inhaler according to claim 1, wherein
the controller determines, for each one-time puff action, whether or not the inhaling condition is satisfied and whether or not the identification condition is satisfied.

3. The non-burning type flavor inhaler according to claim 1, wherein
the controller determines whether or not the identification condition is satisfied after the inhaling condition is satisfied.

4. The non-burning type flavor inhaler according to claim 1, wherein
the controller determines, on the basis of an inclination configured by two or more of the response values or an absolute value of the response value, whether or not at least one of the inhaling condition and the identification condition is satisfied.

5. The non-burning type flavor inhaler according to claim 4, wherein
the inhaling condition is that the absolute value exceeds a predetermined absolute value, and
the identification condition is that the inclination exceeds a predetermined inclination.

6. The non-burning type flavor inhaler according to claim 4, wherein
the inhaling condition is that an absolute value of the response value exceeds a first absolute value, and
the identification condition is that an absolute value of the response value exceeds a second absolute value that is larger than the first absolute value.

7. The non-burning type flavor inhaler according to claim 1, wherein the controller uses a first identification condition as the identification condition in a first puff action, and uses a second identification condition that is different from the first identification condition as the identification condition in a second puff action performed after the first identification condition is satisfied.

8. The non-burning type flavor inhaler according to claim 7, wherein
the controller uses the first identification condition when a specific condition is satisfied after the first identification condition is satisfied.

9. The non-burning type flavor inhaler according to claim 1, wherein
the controller starts a supply of power source output to the atomizer when the identification condition is satisfied.

10. The non-burning type flavor inhaler according to claim 1, wherein
the controller starts a supply of power source output to the atomizer when the inhaling condition is satisfied, and
the controller stops the supply of the power source output to the atomizer when the identification condition is not satisfied after the inhaling condition is satisfied.

11. The non-burning type flavor inhaler according to claim 1, wherein the controller has an action mode by which a supply of power source output to the atomizer is performed on the basis of the response value, and an identification mode by which it is determined, on the basis of the response value, whether or not the identification condition is satisfied, and
the action mode starts after the identification condition is satisfied in the identification mode.

12. The non-burning type flavor inhaler according to claim 11, wherein
in the identification mode, the controller determines whether or not the identification condition is satisfied, on the basis of whether or not a profile represented by two or more of the response values in a space defined by a first axis indicating a dimension of the response value and a second axis indicating a time length corresponds to an identification profile.

13. The non-burning type flavor inhaler according to claim 12, wherein
the identification profile is either registered beforehand or registered by the user.

14. The non-burning type flavor inhaler according to claim 11, wherein
the controller ends the action mode when a profile represented by two or more of the response values in a space defined by a first axis indicating a dimension of the response value and a second axis indicating a time length corresponds to a cancellation profile.

15. The non-burning type flavor inhaler according to claim 11, wherein
the controller resets the identification profile when a profile represented by two or more of the response values in a space defined by a first axis indicating a dimension of the response value and a second axis indicating a time length corresponds to a reset profile.

16. The non-burning type flavor inhaler according to claim 14, wherein
the cancellation profile or the reset profile is the identification profile.

17. The non-burning type flavor inhaler according to claim 12, comprising a notification portion configured to notify a user of the identification profile, the cancellation profile or the reset profile.

18. The non-burning type flavor inhaler according to claim 12, wherein
   the controller determines, on the basis of a stringency selected from among a plurality of stages of stringency, whether or not the profile corresponds to the identification profile, the cancellation profile or the reset profile, and
   the flavor inhaler comprises an operation interface for switching the plurality of stages of stringency.

19. The non-burning type flavor inhaler according to claim 12, wherein the identification profile, the cancellation profile or the reset profile is defined by an absolute value of the response value, by whether or not the response value is a value based on inhaling, by whether or not the response value is a value based on blowing, by a sampling cycle of the response value, or by one or more parameters selected from among these parameters.

20. The non-burning type flavor inhaler according to claim 12, comprising a mouthpiece member configured to be replaceable with respect to the housing, wherein
   the mouthpiece member comprises a memory configured to store the identification profile.

\* \* \* \* \*